United States Patent
Lee et al.

(10) Patent No.: US 10,300,025 B2
(45) Date of Patent: *May 28, 2019

(54) DONEPEZIL TRANSDERMAL DELIVERY SYSTEM

(71) Applicant: Corium, Inc., Menlo Park, CA (US)

(72) Inventors: Eun Soo Lee, Redwood City, CA (US); Amit K. Jain, Milpitas, CA (US); Parminder Singh, Union City, CA (US)

(73) Assignee: Corium, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/660,939

(22) Filed: Jul. 26, 2017

(65) Prior Publication Data

US 2018/0028462 A1    Feb. 1, 2018

Related U.S. Application Data

(60) Provisional application No. 62/504,408, filed on May 10, 2017, provisional application No. 62/504,391, (Continued)

(51) Int. Cl.
*A61K 9/70* (2006.01)
*A61K 31/445* (2006.01)
(Continued)

(52) U.S. Cl.
CPC .......... *A61K 9/7038* (2013.01); *A61K 9/7023* (2013.01); *A61K 9/7053* (2013.01);
(Continued)

(58) Field of Classification Search
CPC .... A61K 31/445; A61K 9/7084; A61K 47/10; A61K 47/12; A61K 47/32
See application file for complete search history.

(56) References Cited

U.S. PATENT DOCUMENTS 3,391,142 A    7/1968   Mills et al.
3,546,141 A    12/1970  Washburn et al.
(Continued)

FOREIGN PATENT DOCUMENTS

CN    102048678 A    5/2011
CN    105693556 A    6/2016
(Continued)

OTHER PUBLICATIONS

US 9,095,635 B1, 08/2015, Willman et al. (withdrawn)
(Continued)

*Primary Examiner* — Jianfeng Song
(74) *Attorney, Agent, or Firm* — McDermott Will & Emery LLP; Judy M. Mohr

(57) ABSTRACT

A transdermal delivery system for systemic delivery of donepezil is described, where the system comprises an adhesive matrix drug reservoir layer comprised of a copolymer of acrylic acid/vinyl acetate, triethyl citrate, and donepezil base generated in situ by reaction of donepezil HCl and an alkaline salt. The system is provided for treatment of Alzheimer's disease, and achieves transdermal delivery of the therapeutic agent at steady state that is bioequivalent to administration of the therapeutic agent orally.

14 Claims, 8 Drawing Sheets

Related U.S. Application Data filed on May 10, 2017, provisional application No. 62/457,794, filed on Feb. 10, 2017, provisional application No. 62/444,763, filed on Jan. 10, 2017, provisional application No. 62/444,745, filed on Jan. 10, 2017, provisional application No. 62/423,133, filed on Nov. 16, 2016, provisional application No. 62/367,542, filed on Jul. 27, 2016, provisional application No. 62/367,502, filed on Jul. 27, 2016.

(51) Int. Cl.

| | | |
|---|---|---|
| *A61K 47/32* | (2006.01) | |
| *A61K 47/12* | (2006.01) | |
| *A61K 47/10* | (2017.01) | |
| *A61K 31/00* | (2006.01) | |
| *A61K 47/02* | (2006.01) | |
| *C08K 5/00* | (2006.01) | |
| *A61K 31/13* | (2006.01) | |
| *A61K 31/137* | (2006.01) | |
| *A61K 31/18* | (2006.01) | |
| *A61K 31/27* | (2006.01) | |
| *A61K 31/045* | (2006.01) | |

(52) U.S. Cl.
CPC .......... *A61K 9/7061* (2013.01); *A61K 9/7084* (2013.01); *A61K 9/7092* (2013.01); *A61K 31/00* (2013.01); *A61K 31/13* (2013.01); *A61K 31/137* (2013.01); *A61K 31/18* (2013.01); *A61K 31/27* (2013.01); *A61K 31/445* (2013.01); *A61K 47/02* (2013.01); *A61K 47/10* (2013.01); *A61K 47/12* (2013.01); *A61K 47/32* (2013.01); *C08K 5/0016* (2013.01); *A61K 31/045* (2013.01)

(56) References Cited

U.S. PATENT DOCUMENTS

| | | |
|---|---|---|
| 3,549,016 A | 12/1970 | Rigopulos |
| 4,122,193 A | 10/1978 | Scherm et al. |
| 4,273,774 A | 6/1981 | Scherm |
| 4,781,924 A | 11/1988 | Lee et al. |
| 4,837,027 A | 6/1989 | Lee et al. |
| 4,886,812 A | 12/1989 | Griss et al. |
| 4,895,841 A | 1/1990 | Sugimoto et al. |
| 5,026,556 A | 6/1991 | Drust et al. |
| 5,061,703 A | 10/1991 | Bormann et al. |
| 5,123,900 A | 6/1992 | Nick |
| 5,252,588 A * | 10/1993 | Azuma ................ A61K 9/0014 424/449 |
| 5,424,077 A | 6/1995 | Lajoie |
| 5,614,560 A | 3/1997 | Lipton |
| 5,866,585 A | 2/1999 | Fogel |
| 5,958,919 A | 9/1999 | Olney et al. |
| 6,004,578 A | 12/1999 | Lee et al. |
| 6,255,348 B1 | 7/2001 | Elstner |
| 6,383,471 B1 | 5/2002 | Chen et al. |
| 6,512,010 B1 | 1/2003 | Gale et al. |
| 6,521,639 B1 | 2/2003 | Murahashi et al. |
| 6,746,689 B2 | 6/2004 | Fischer et al. |
| 6,923,988 B2 | 8/2005 | Patel et al. |
| 6,929,801 B2 | 8/2005 | Klose et al. |
| 7,097,853 B1 | 8/2006 | Garbe et al. |
| 7,176,185 B2 | 2/2007 | Hilfinger et al. |
| 7,250,394 B2 | 7/2007 | Nedergaard |
| 7,320,802 B2 | 1/2008 | Ryde et al. |
| 7,335,379 B2 | 2/2008 | Carrara et al. |
| 7,462,743 B2 | 12/2008 | Merli et al. |
| 7,670,838 B2 | 3/2010 | Deisseroth et al. |
| 7,682,628 B2 | 3/2010 | Singh |
| 7,858,114 B2 | 12/2010 | Ito |
| 7,888,422 B2 | 2/2011 | Jackson et al. |
| 8,058,291 B2 | 11/2011 | Went et al. |
| 8,168,209 B2 | 5/2012 | Went et al. |
| 8,246,978 B2 | 8/2012 | Kydonieus et al. |
| 8,252,321 B2 | 8/2012 | Dipierro et al. |
| 8,283,379 B2 | 10/2012 | Went et al. |
| 8,362,085 B2 | 1/2013 | Went et al. |
| 8,512,742 B2 | 8/2013 | Amano et al. |
| 8,614,274 B2 | 12/2013 | Jackson et al. |
| 8,673,338 B2 | 3/2014 | Bleier |
| 8,784,879 B2 | 7/2014 | Singh et al. |
| 8,815,281 B2 | 8/2014 | Kanios et al. |
| 8,840,922 B2 | 9/2014 | Kawakami et al. |
| 8,840,935 B2 | 9/2014 | Haber et al. |
| 8,874,879 B2 | 10/2014 | Ge et al. |
| 9,012,511 B2 | 4/2015 | Neville et al. |
| 9,248,104 B2 | 2/2016 | Valia et al. |
| 9,622,986 B2 | 4/2017 | Im et al. |
| 9,993,466 B2 | 6/2018 | Lee et al. |
| 10,016,372 B2 | 7/2018 | Singh et al. |
| 2001/0031787 A1 * | 10/2001 | Hsu ................ A61K 9/0014 514/534 |
| 2002/0192243 A1 | 12/2002 | Hsu et al. |
| 2003/0170308 A1 | 9/2003 | Cleary et al. |
| 2004/0022835 A1 | 2/2004 | Pai et al. |
| 2004/0087658 A1 | 5/2004 | Moebius |
| 2005/0113458 A1 | 5/2005 | Gupta et al. |
| 2006/0035888 A1 | 2/2006 | Jonas et al. |
| 2006/0205822 A1 | 9/2006 | Jonas et al. |
| 2008/0038328 A1 | 2/2008 | Higo et al. |
| 2008/0107719 A1 | 5/2008 | Likitlersuang et al. |
| 2008/0131490 A1 * | 6/2008 | Hanatani ............ A61K 9/7061 424/448 |
| 2008/0131491 A1 | 6/2008 | Hanatani et al. |
| 2008/0138388 A1 * | 6/2008 | Aida .................... A61K 9/7061 424/448 |
| 2009/0081259 A1 | 3/2009 | Jonas et al. |
| 2009/0124659 A1 | 5/2009 | Moebius |
| 2009/0156639 A1 | 6/2009 | Trippodi-Murphy et al. |
| 2009/0175929 A1 * | 7/2009 | Terahara ............ A61K 9/7053 424/449 |
| 2010/0178037 A1 | 7/2010 | Chen et al. |
| 2010/0178307 A1 * | 7/2010 | Wen .................... A61K 9/7084 424/400 |
| 2010/0227852 A1 | 9/2010 | Moebius |
| 2011/0059141 A1 | 3/2011 | Ito |
| 2011/0059169 A1 | 3/2011 | Went et al. |
| 2011/0313372 A1 | 12/2011 | Eifler et al. |
| 2012/0245537 A1 | 9/2012 | Horstmann et al. |
| 2013/0053358 A1 | 2/2013 | Aida et al. |
| 2014/0062081 A1 | 2/2014 | Yang et al. |
| 2014/0256690 A1 | 9/2014 | Arkady et al. |
| 2014/0322284 A1 | 10/2014 | Singh et al. |
| 2014/0370076 A1 | 12/2014 | Choi et al. |
| 2015/0098980 A1 | 4/2015 | Pongpeerepat et al. |
| 2016/0051486 A1 | 2/2016 | Choi et al. |
| 2018/0028461 A1 | 2/2018 | Singh et al. |
| 2018/0028463 A1 | 2/2018 | Lee et al. |
| 2018/0028466 A1 | 2/2018 | Lee et al. |
| 2018/0028467 A1 | 2/2018 | Singh et al. |
| 2018/0028512 A1 | 2/2018 | Lee et al. |
| 2018/0028663 A1 | 2/2018 | Lee et al. |
| 2018/0185298 A1 | 7/2018 | Jain et al. |
| 2018/0235901 A1 | 8/2018 | Lee et al. |

FOREIGN PATENT DOCUMENTS

| | | |
|---|---|---|
| EP | 0540623 B1 | 9/1994 |
| EP | 1423100 A1 | 6/2004 |
| EP | 2098233 A1 | 9/2006 |
| EP | 1682109 B1 | 10/2008 |
| EP | 2016941 A1 | 1/2009 |
| EP | 2090310 A1 | 8/2009 |
| EP | 2098235 A1 | 9/2009 |
| EP | 2260839 A2 | 12/2010 |
| EP | 2514415 A1 | 10/2012 |
| EP | 2638906 A1 | 9/2013 |
| JP | 2009203213 * | 9/2009 |
| WO | WO 1996/040087 A2 | 12/1996 |

(56) References Cited

FOREIGN PATENT DOCUMENTS

| WO | WO 2003/020248 A1 | 3/2003 |
|---|---|---|
| WO | WO 2005/079779 A1 | 9/2005 |
| WO | WO 2010/051349 A1 | 5/2010 |
| WO | WO 2011/070361 A1 | 6/2011 |
| WO | WO 2011/081628 A1 | 7/2011 |
| WO | WO 2012/084969 A1 | 6/2012 |
| WO | WO 2012/097197 A1 | 7/2012 |
| WO | WO 2015/053878 A1 | 4/2015 |
| WO | WO 2015/200472 A1 | 12/2015 |
| WO | WO 2016/099198 A1 | 6/2016 |
| WO | WO 2016/209982 A1 | 12/2016 |
| WO | WO 2017/018321 A1 | 2/2017 |
| WO | WO 2017/117554 A1 | 7/2017 |
| WO | WO 2017/223402 A1 | 12/2017 |
| WO | WO 2018/022814 A1 | 2/2018 |
| WO | WO 2018/022815 A1 | 2/2018 |
| WO | WO 2018/022816 A1 | 2/2018 |
| WO | WO 2018/022817 A1 | 2/2018 |
| WO | WO 2018/022818 A1 | 2/2018 |

OTHER PUBLICATIONS

Ashall, "Tobacco Facts #4: Smokers are freebasing nicotine!—The Great Tobacco Plague", Dr Frank Ashalls Blog, Retreived from the Internet: https://biochemdr1.wordpress.com/2013/11/30/tobacco-fact-4-somkers-are-freebasing-nicotine/, 7 pages (Nov. 30, 2013).
International Search Report from International Patent Application No. PCT/US2017/044047 dated Nov. 3, 2017.
Partial International Search Report from International Patent Application No. PCT/US2017/044048 dated Nov. 3, 2017.
International Search Report from International Patent Application No. PCT/US2017/044049 dated Nov. 7, 2017.
International Search Report from International Patent Application No. PCT/US2017/044050 dated Nov. 6, 2017.
International Search Report from International Patent Application No. PCT/US2017/044051 dated Nov. 2, 2017.
Aida et al., "Adhesive patch useful in pharmaceuticals, for delivering drugs, provides single surface of support with adhesive layer; where adhesive layer contains drug in solution stae and crystalline state", Database WPI, AN 2008-F37689 (2013).
Brantseva et al., "Rheological and adhesive properties of PIB-based pressure-sensitive adhesives with montmorillonite-type nanofillers", European Polymer Journal, vol. 76, pp. 228-244 (2016).
Chladek et al., "Steady-state bioequivalence studies of two memantine tablet and oral solution formulations in healthy volunteers", J. Appl. Biomed., vol. 6, pp. 39-45 (2008).
Choi et al., "Effect of fatty acids on the transdermal delivery of donepezil: in vitro and in vivo evaluation", Int. J. Pharm., vol. 422, No. 1-2; pp. 83-90 (2012).
Del Rio-Sancho, "Transdermal absorption of memantin—effect of chemical enhancers, iontophoresis, and role of enhancer lipophilicity", Eur J. Pharm. Biopharm., vol. 82, No. 1, pp. 164-170 (2012).
Fang et al., "Donepezil percutaneous absorption enhancer and back lining layer which includes polyethylene, polyester and ethylene-vinyl acetate copolymer", Database WPI, AN 2013-G75464 (2013).
Forchetti, "Treating patients with moderate to severe Alzheimer's disease: implications of recent pharmacologic studies", Prim. Care Companion J. Clin. Psychiatry., vol. 7, No. 4, pp. 155-161 (2005).
Fornasari et al., "Synthesis and antioxidant properties of novel memantine derivatives", Cent. Nerv. Syst. Agents Med. Chem., vol. 17, No. 2, pp. 123-128 (2017).
International Search Report from International Application No. PCT/US2016/038792 dated Sep. 27, 2016.
Kato, Patch used for treating Alzheimer-type dementia, comprises support portion, adhesive layer, donepezil and/or its hydrochloride, and additive chosen from isostearic acid, 2-cetyl ethylhexanoate, and hexadecyl isostearate, Database WPI, AN 2014-C88308 (2014).
Pastore et al., "Transdermal patches: history, development and pharmacology", Br. J. Pharmacol., vol. 172, No. 9, pp. 2179-2209 (2015).
Ravi and Gupta, "The treatment of alzheimers disease by using donepzil loaded transdermal patch", J. Chem. Pharm. Res., vol. 7, No. 3, pp. 806-813 (2015).
Schulz et al., "Therapeutic and toxic blood concentrations of nearly 1,000 drugs and other xenobiotics", Crit. Care, vol. 16, No. R136, 4 pgs. (2012).
Sozio et al., "Transdermal donepezil on the treatment of Alzheimer's disease", Neuropsychiatr. Dis. Treat., vol. 8, pp. 361-368 (2012).
Tiseo et al., "Pharmacokinetic and pharmacodynamic profile of donepezil HCl following evening administration", Br. J. Pharmacol., vol. 46, Suppl. 1, pp. 13-18 (1998).
International Search Report from International Patent Application No. PCT/US2017/038934 dated Oct. 10, 2017.

* cited by examiner

DONEPEZIL TRANSDERMAL DELIVERY SYSTEM

CROSS-REFERENCE TO RELATED APPLICATIONS

This application claims the benefit of U.S. Provisional Application No. 62/504,408, filed May 10, 2017; U.S. Provisional Application No. 62/504,391, filed May 10, 2017; U.S. Provisional Application No. 62/457,794, filed Feb. 10, 2017; U.S. Provisional Application No. 62/444,763, filed Jan. 10, 2017; U.S. Provisional Application No. 62/444,745, filed Jan. 10, 2017; U.S. Provisional Application No. 62/423,133, filed Nov. 16, 2016; U.S. Provisional Application No. 62/367,542, filed Jul. 27, 2016; and U.S. Provisional Application No. 62/367,502, filed Jul. 27, 2016, each incorporated herein by reference in its entirety.

TECHNICAL FIELD

The subject matter described herein relates to a transdermal delivery system manufactured with a donepezil salt for systemic delivery of donepezil.

BACKGROUND

Donepezil is an acetylcholinesterase inhibitor with the chemical structure 2,3-Dihydro-5,6-dimethoxy-2-[[1-(phenylmethyl)-4-piperidinyl]methyl]-1H-inden-1-one:

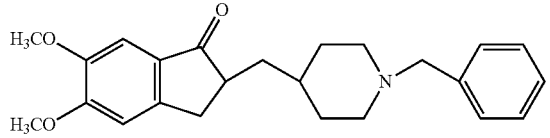

Donepezil has a molecular weight of 379.5 and is lipophilic (Log P value 3.08-4.11).

An oral tablet of donepezil hydrochloride (ARICEPT®) is approved in the U.S. for use in treating Alzheimer's dementia. Due to the nature of cognitive disorders, oral medications may be subject to problems with patient compliance especially for formulations that need to be taken throughout the day. Delivery of medications by transdermal, injection, or rectal routes to patients suffering from cognitive disorders has been investigated. U.S. Pat. No. 7,858,114 describes a percutaneous absorption preparation of donepezil for use as a plaster for long term delivery of an anti-dementia drug. U.S. Patent No. 2014/0370076 describes a transdermal drug delivery system comprising donepezil or a salt thereof that uses an acrylate-rubber hybrid adhesive that is prepared by a process without n-hexane. U.S. Pat. No. 4,895,841 to Eisai Co., Ltd. describes cyclic amine compounds including donepezil for use in treating dementia including Alzheimer senile dementia, Huntington's chorea, Pick's disease, and ataxia. Other transdermal delivery systems proposed use an overlay or other rate-limiting membrane to control delivery of the drug from the transdermal device, see e.g. U.S. Published Application No. 2010/0178307 which describes the use of a first and second overlay. Despite these teachings, there are no donepezil transdermal patches or devices available in the United States.

Delivery of anti-dementia drugs over a long period of time (e.g. several days or more) is difficult. Transdermal delivery of basic drugs including donepezil can be especially difficult due to poor skin permeability. Further, some active agents have poor or low solubility in the adhesives and/or other components used in typical transdermal formulations. Further, there is a need for stable, long term administration of anti-dementia agents (e.g. 1-10 days or more) that provides a stable and effective release of the agent over the administration period and has suitable adhesion for the long term administration.

Therefore, there exists a need for transdermal compositions, devices and methods that address these shortcomings.

The foregoing examples of the related art and limitations related therewith are intended to be illustrative and not exclusive. Other limitations of the related art will become apparent to those of skill in the art upon a reading of the specification and a study of the drawings.

BRIEF SUMMARY

The following aspects and embodiments thereof described and illustrated below are meant to be exemplary and illustrative, not limiting in scope.

In one aspect, a transdermal delivery system for systemic delivery of donepezil is provided. The system comprises a skin contact adhesive layer to attach the system to the skin of a user, and a drug reservoir comprised of (i) a solvent composition comprising glycerin and one or more of lauryl lactate, sorbitan monolaurate and triethyl, and (ii) donepezil base generated in situ by reaction of donepezil HCl and an alkaline salt. In one embodiment, the drug reservoir further comprises an acrylate copolymer.

In one embodiment, the system further comprises an intermediate layer that, in one embodiment, is directly on the contact adhesive layer and disposed between the contact adhesive layer and the drug reservoir. In one embodiment, the intermediate layer is a microporous membrane comprising a plurality of pores. In another embodiment, the plurality of pores in the microporous membrane contains a solvent composition comprised of one or more of triethyl citrate, sorbitan monolaurate, and lauryl lactate.

In another aspect, a transdermal delivery system for systemic delivery of donepezil is provided. The system comprises, in series from the skin facing side to the external environment, a skin contact adhesive layer to attach the system to the skin of a user, the skin contact adhesive layer optionally manufactured from an adhesive formulation that does not comprise donepezil base or a donepezil salt. Directly in contact with the skin contact adhesive layer is an intermediate layer. On the opposing surface of the intermediate layer is a drug reservoir layer comprised of glycerin, and donepezil base generated in situ by reaction of donepezil HCl and an alkaline salt.

In one embodiment, the drug reservoir additionally comprises a copolymer of acrylic acid/vinyl acetate.

In other embodiments, the transdermal system additionally comprises a first backing layer, and in contact with the first backing layer is an adhesive overlay. A second backing layer may be in contact with the adhesive overlay and with the environment.

In one embodiment, the skin contact adhesive layer is comprised of a copolymer of acrylic acid/vinyl acetate.

In another embodiment, the skin contact adhesive layer additionally comprises crosslinked polyvinylpyrrolidone.

In yet another embodiment, the skin contact adhesive layer comprises a skin contact adhesive layer solvent composition that comprises one or more solvents selected from the group consisting of triethyl citrate, sorbitan monolaurate, and lauryl lactate. In still another embodiment, contact adhesive layer solvent composition comprises at least two of triethyl citrate, sorbitan monolaurate, and lauryl lactate. In another embodiment, the contact adhesive layer solvent composition comprises triethyl citrate, sorbitan monolaurate, and lauryl lactate.

In one embodiment, the intermediate layer is a rate controlling membrane for donepezil base.

In another embodiment, the rate controlling membrane is a microporous polypropylene.

In yet another embodiment, the intermediate layer is a non-woven polyester.

In one embodiment, the alkaline salt in the drug reservoir layer is sodium bicarbonate.

In another embodiment, the drug reservoir layer additionally comprises triethyl citrate.

In still another embodiment, the drug reservoir layer additionally comprises one or both of sorbitan monolaurate and lauryl lactate.

In yet another embodiment, the adhesive overlay is comprised of a polyisobutylene and polybutene mixture. In another embodiment, embodiment, the adhesive overlay is comprised of a single layer or a single-ply layer of an acrylate adhesive.

In one embodiment, the adhesive overlayer is comprised of a first layer and a second layer, the first layer composed of a polyisobutylene, polybutene and crosslinked polyvinylpyrrolidone mixture and the second layer composed of an acrylic adhesive.

In another aspect, a composition comprising (i) donepezil base generated in situ by reaction of donepezil HCl and an alkaline salt; (ii) glycerin (glycerol) and, optionally, (iii) a copolymer of acrylic acid/vinyl acetate, is provided.

In one embodiment, the drug reservoir comprises triethyl citrate.

In another embodiment, the drug reservoir comprises sorbitan monolaurate.

In still another embodiment, the drug reservoir comprises a crosslinked polyvinylpyrrolidone.

In yet another embodiment, the alkaline salt is selected from the group consisting of sodium carbonate, sodium bicarbonate, potassium carbonate, potassium bicarbonate, trisodium phosphate, disodium hydrogen phosphate, sodium oxylate, sodium succinate, sodium citrate, and sodium salicylate.

In another aspect, a composition consisting essentially of donepezil base generated in situ by reaction of donepezil HCl and sodium bicarbonate; a permeation enhancer mixture of triethyl citrate, sorbitan monolaurate, and glycerin; and a polymeric, adhesive matrix of crosslinked polyvinylpyrrolidone and a copolymer of acrylic acid/vinyl acetate is provided.

In yet another aspect, a composition consisting essentially of donepezil base generated in situ by reaction of between about 5-25 wt % donepezil HCl and between about 1-5 wt % sodium bicarbonate; about 0-15 wt % triethyl citrate; about 0-5 wt % sorbitan monolaurate; about 5-15 wt % glycerin; about 1-10 wt % lauryl lactate; about 5-25 wt % crosslinked polyvinylpyrrolidone; and about 30-50 wt % acrylate-vinylacetate copolymer is provided.

In yet another aspect, a composition consisting essentially of donepezil base generated in situ by reaction of between about 10-25 wt % donepezil HCl and between about 1-5 wt % sodium bicarbonate; about 5-15 wt % triethyl citrate; about 0.5-5 wt % sorbitan monolaurate; about 5-15 wt % glycerin; about 1-10 wt % lauryl lactate; about 5-25 wt % crosslinked polyvinylpyrrolidone; and about 30-50 wt % acrylate-vinylacetate copolymer is provided.

In still another aspect, a composition consisting essentially of donepezil base generated in situ by reaction of between about 14-18 wt % donepezil HCl and between about 2-5 wt % sodium bicarbonate; about 8-12 wt % triethyl citrate; about 1.5-2.5 wt % sorbitan monolaurate; about 9-11 wt % glycerin; about 1-10 wt % lauryl lactate; about 13-17 wt % crosslinked polyvinylpyrrolidone; and about 40-42 wt % acrylate-vinylacetate copolymer is provided.

In still another aspect, a composition consisting essentially of donepezil base generated in situ by reaction of between about 10-18 wt % donepezil HCl and between about 1-5 wt % sodium bicarbonate; about 8-12 wt % triethyl citrate; about 1.5-2.5 wt % sorbitan monolaurate; about 9-11 wt % glycerin; about 1-10 wt % lauryl lactate; about 13-17 wt % crosslinked polyvinylpyrrolidone; and about 40-42 wt % acrylate-vinylacetate copolymer is provided.

In yet another aspect, a transdermal device or a composition is comprised of the compositions as described herein, a rate controlling membrane or a non-woven layer; and a skin contact adhesive is provided.

In one embodiment, the rate controlling membrane is a microporous polypropylene membrane.

In one embodiment, the microporous membrane has a plurality of pores, where the plurality of pores contains a solvent composition comprised of one or more of triethyl citrate, sorbitan monolaurate, and lauryl lactate.

In another embodiment, a skin contact adhesive comprises triethyl citrate, an α-hydroxy acid, or both.

In yet another embodiment, the α-hydroxy acid is an ester of lactic acid or glycolic acid.

In one embodiment, the α-hydroxy acid is lauryl lactate.

In another aspect, a method for treating Alzheimer's disease is provided, wherein a transdermal delivery system or a composition or a system comprising a composition as described herein is provided for administration to the skin of a patient.

In another aspect, a method for delivering a therapeutic agent to a subject is provided, the method comprising providing a transdermal delivery system as described herein or a transdermal delivery system comprising a composition as described herein, and administering or instructing to administer the transdermal delivery system to the skin of a subject. The administering achieves transdermal delivery of the therapeutic agent that is bioequivalent to administration of the therapeutic agent orally, wherein bioequivalency is established by (a) a 90% confidence interval of the relative mean Cmax and AUC of the therapeutic agent administered from the transdermal delivery system and via oral delivery between 0.70 and 1.43 or between 0.80 and 1.25, or (b) a 90% confidence interval of the geometric mean ratios for AUC and Cmax of the therapeutic agent administered from the transdermal delivery system and via oral delivery between 0.70 and 1.43 or between 0.80 and 1.25.

In one embodiment, bioequivalency is established in healthy subjects.

In another embodiment, bioequivalency is established in a fasting condition. In one embodiment, bioequivalency is established in a fed or non-fasting condition.

In still another embodiment, bioequivalency is established using the same dose of therapeutic agent given orally and transdermally. In another embodiment, the dose of therapeutic agent given transdermally is within about 5%, 10%, or 15% of the dose given orally.

In yet another embodiment, the chronic condition is Alzheimer's disease.

In still another embodiment, the administering or instructing to administer comprises administering or instructing to administer once weekly.

In an embodiment, the transdermal delivery system comprises a dose of donepezil base to provide between 0.05-25 mg/24 hours, 0.1-25 mg/24 hours, 1-25 mg/24 hours or between 5-10 mg/24 hours.

In addition to the exemplary aspects and embodiments described above, further aspects and embodiments will become apparent by reference to the drawings and by study of the following descriptions.

Additional embodiments of the present systems, methods and compositions, and the like, will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1A:
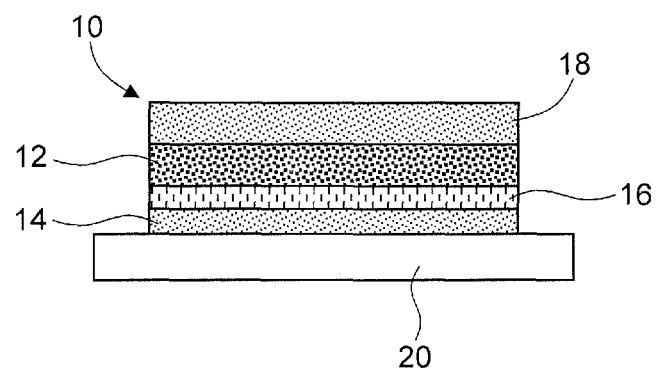
FIGS. 1A-1D are illustrations of transdermal delivery systems according to several embodiments.

Various aspects now will be described more fully hereinafter. Such aspects may, however, be embodied in many different forms and should not be construed as limited to the embodiments set forth herein; rather, these embodiments are provided so that this disclosure will be thorough and complete, and will fully convey its scope to those skilled in the art.

Where a range of values is provided, it is intended that each intervening value between the upper and lower limit of that range and any other stated or intervening value in that stated range is encompassed within the disclosure. For example, if a range of 1 µm to 8 µm is stated, it is intended that 2 µm, 3 µm, 4 µm, 5 µm, 6 µm, and 7 µm are also explicitly disclosed, as well as the range of values greater than or equal to 1 µm and the range of values less than or equal to 8 µm.

The singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

The word "about" when immediately preceding a numerical value means a range of plus or minus 10% of that value, e.g., "about 50" means 45 to 55, "about 25,000" means 22,500 to 27,500, etc., unless the context of the disclosure indicates otherwise, or is inconsistent with such an interpretation. For example in a list of numerical values such as "about 49, about 50, about 55, "about 50" means a range extending to less than half the interval(s) between the preceding and subsequent values, e.g., more than 49.5 to less than 52.5. Furthermore, the phrases "less than about" a value or "greater than about" a value should be understood in view of the definition of the term "about" provided herein.

The terms "drug" or "active agent" or "therapeutically active agent" are used interchangeably.

An "adhesive matrix" as described herein includes matrices made in one piece, for example, matrices made via solvent casting or extrusion as well as matrices formed in two or more portions that are then pressed or joined together.

"Donepezil" as used herein refers to 2,3-dihydro-5,6-dimethoxy-2-[[1-(phenylmethyl)-4-piperidinyl]methyl]-1H-inden-1-one.

The terms "treatment," "therapy," "therapeutic" and the like, as used herein, encompass any course of medical intervention aimed at a pathologic condition, and includes not only permanent cure of a disease, but prevention of disease, control or even steps taken to mitigate a disease or disease symptoms.

The term "skin" as used herein refers to skin or mucosal tissue, including the interior surface of body cavities that have a mucosal lining. The term "skin" should be interpreted as including "mucosal tissue" and vice versa.

The term "therapeutically effective amount" as used herein refers to the amount of an active agent that is nontoxic but sufficient to provide the desired therapeutic effect. The amount that is "effective" will vary from subject to subject, depending on the age and general condition of the individual, the particular active agent or agents, and the like as known to those skilled in the art.

The phrase "pharmaceutically acceptable" is employed herein to refer to those compounds, salts, compositions, dosage forms, etc., which are—within the scope of sound medical judgment—suitable for use in contact with the tissues of human beings and/or other mammals without excessive toxicity, irritation, allergic response, or other problem or complication, commensurate with a reasonable benefit/risk ratio. In some aspects, "pharmaceutically acceptable" means approved by a regulatory agency of the federal or a state government, or listed in the U.S. Pharmacopeia or other generally recognized pharmacopeia for use in mammals (e.g., animals), and more particularly, in humans.

The terms "transdermal" or "transdermal delivery" as used herein refer to administration of an active agent to a body surface of an individual so that the agent passes through the body surface, e.g., skin, and into the individual's blood stream. The term "transdermal" is intended to include transmucosal administration, i.e., administration of a drug to the mucosal (e.g., sublingual, buccal, vaginal, rectal) surface of an individual so that the agent passes through the mucosal tissue and into the individual's blood stream.

The term "treating" is used herein, for instance, in reference to methods of treating a disorder, such as Alzheimer's disease, and generally includes the administration of a compound or composition which reduces the frequency of, or delays the onset of, symptoms of a medical condition (e.g., Alzheimer's disease) in a subject relative to a subject not receiving the compound or composition. This can include reversing, reducing, or arresting the symptoms, clinical signs, and underlying pathology of a condition in a manner to improve or stabilize a subject's condition (e.g., regression of mental facilities).

The compositions of the present disclosure can comprise, consist essentially of, or consist of, the components disclosed.

All percentages, parts and ratios are based upon the total weight of the topical compositions and all measurements made are at about 25° C., unless otherwise specified.

By reserving the right to proviso out or exclude any individual members of any such group, including any sub-ranges or combinations of sub-ranges within the group, that can be claimed according to a range or in any similar manner, less than the full measure of this disclosure can be claimed for any reason. Further, by reserving the right to proviso out or exclude any individual substituents, analogs, compounds, ligands, structures, or groups thereof, or any members of a claimed group, less than the full measure of this disclosure can be claimed for any reason.

Throughout this disclosure, various patents, patent applications and publications are referenced. The disclosures of these patents, patent applications and publications in their entireties are incorporated into this disclosure by reference in order to more fully describe the state of the art as known to those skilled therein as of the date of this disclosure. This disclosure will govern in the instance that there is any inconsistency between the patents, patent applications and publications cited and this disclosure.

For convenience, certain terms employed in the specification, examples and claims are collected here. Unless defined otherwise, all technical and scientific terms used in this disclosure have the same meanings as commonly understood by one of ordinary skill in the art to which this disclosure belongs.

II. Transdermal Delivery System and Compositions for Use in a Transdermal Delivery System A transdermal delivery system for systemic delivery of donepezil base is provided. The transdermal system in general is comprised of a skin contact adhesive and a drug reservoir. In one embodiment, the system additionally comprises an intermediate layer that is typically a fabric or membrane or other non-adhesive material, situated between the drug reservoir and the skin contact adhesive. The compositions of the layers in the system are now described.

The drug reservoir, in one embodiment, is a composition comprising a solvent mixture and donepezil base generated in situ by reaction of a donepezil salt and an alkaline salt. The drug reservoir is manufactured using a salt form of donepezil, e.g., donepezil hydrochloride (HCl) and an alkaline salt, that react in situ to form donepezil base. The alkaline salt can be, for example, sodium carbonate, sodium bicarbonate, potassium carbonate, potassium bicarbonate, trisodium phosphate, disodium hydrogen phosphate, sodium oxylate, sodium succinate, sodium citrate, or sodium salicylate.

The solvent composition in the drug reservoir may comprise a hydrophilic solvent in which the salt form of the active agent (e.g. donepezil hydrochloride) is soluble, a permeation enhancer, and other solvents. In one embodiment, the hydrophilic solvent for solubilizing the salt form of the active agent is a hydrophilic solvent selected from polyethylene glycol, propylene glycol, glycerin (glycol), acetonitrile, 1-propanol, N,N-dimethylformamide and dimethyl sulfoxide. In one embodiment, and as illustrated in the working examples herein, the hydrophilic solvent is glycerin. In some embodiments, an α-hydroxy acid as a skin penetration enhancer is present. Enhancers in the form of α-hydroxy acid are preferably an ester of lactic acid or glycolic acid, and an example is lauryl lactate. The solvent composition, in another embodiment, also comprises triethyl citrate, and in other embodiments, one or both of glycerin and sorbitan (mono)laurate are additionally present.

The drug reservoir is, in one embodiment, a polymeric adhesive layer. The adhesive layer can be formed of any of a variety of adhesive materials, such as pressure sensitive adhesive polymers. Polyacrylate pressure sensitive adhesive polymers are an example, and typically comprise a polyacrylate that is a polymer or a copolymer of a monomer or monomers selected from acrylic acid esters and methacrylic acid esters. Other monomers, such as acrylic acid and vinyl acetate, may be present. In embodiments, the acrylic polymer is based on acrylic esters such as 2-ethylhexyl acrylate (2-EHA) and ethyl acrylate. In some embodiments, the polyacrylate polymer is a polymer or a copolymer of a monomer or monomers selected from acrylic acid and vinyl acetate. In embodiments, the acrylic polymer adhesive has pendent carboxyl (—COOH) or hydroxyl (—OH) functional groups. In embodiments, the acrylic polymer adhesive comprises at least one of polyacrylate, polymethacrylate, derivatives thereof, and co-polymers thereof. In embodiments, the acrylic adhesive is comprised of an acrylate copolymer comprising acrylic ester monomers, acrylic acid, and/or vinyl acetate monomers. A copolymer of acrylic acid and vinyl acetate is one example. Acrylate copolymers are sold under the trade-name DURO-TAK® and include, but are not limited to, DURO-TAK® 387-2516, 387-2051, 387-2287 and 387-2074.

The drug reservoir may also comprise a copolymer such as a polyvinylpyrrolidone/vinyl acetate copolymer, an acrylic acid/vinyl acetate copolymer, or a vinyl acetate/ethylene acetate copolymer. In one embodiment, the copolymer is a vinyl acetate/N-vinylpyrrolidone copolymer such as the copolymer sold as Plasdone™ S630 (Ashland). In another embodiment, the polyvinylpyrrolidone-vinyl acetate copolymer is a linear random copolymer of n-vinyl-2-pyrrolidone and vinyl acetate. In one embodiment, the copolymer is a 60:40 copolymer of n-vinyl-2-pyrrolidone and vinyl acetate.

The drug reservoir may also comprise a polyvinylpyrrolidone (PVP). PVP is a water-soluble polymer comprised of the N-vinylpyrrolidone monomer, and is available in various forms, including cross-linked and non-crosslinked. In some of the working examples herein, a cross-linked PVP is included in the adhesive matrix drug reservoir.

In some embodiments, the drug reservoir comprises at least about 25-80 wt % of adhesive polymers relative to the weight of the drug reservoir (inclusive of sub-ranges). In embodiments, the drug reservoir comprises at least about 35-80%, at least about 30-65%, at least about 30-75%, at least about 40-75%, at least about 50-75%, at least about 60-75%, at least about 25-70%, at least about 30-70%, at least about 40-70%, at least about 50-70%, at least about 60-70%, at least about 25-60%, at least about 30-60%, at least about 40-60%, at least about 50-60%, at least about 25-50%, at least about 30-50%, at least about 40-50%, at least about 25-40%, at least about 30-40%, or at least about 25-30% of an adhesive polymer or copolymer or mixture of polymers and/or copolymers (all percentages in wt %). It will be appreciated that the drug reservoir adhesive matrix may include one or more or at least one adhesive polymers or copolymers. In embodiments, the adhesive matrix drug reservoir comprises at least about 5-75% of an individual polymer relative to the total weight of the polymers in the matrix. In embodiments, the adhesive matrix drug reservoir comprises at least about 5-10%, 5-15%, 5-20%, 5-25%, 5-30%, 5-40%, 5-50%, 5-60%, 5-70%, 5-75%, 10-15%, 10-20%, 10-20%, 10-25%, 10-30%, 10-40%, 10-50%, 10-60%, 10-70%, 10-75%, 15-20%, 15-25%, 15-30%, 15-40%, 15-50%, 15-60%, 15-70%, 15-75%, 20-25%, 20-30%, 20-40%, 20-50%, 20-60%, 20-70%, 20-75%, 25-30%, 25-40%, 25-50%, 25-60%, 25-70%, 25-75%, 30-40%, 30-50%, 30-60%, 30-70%, 30-75%, 40-50%, 40-60%, 40-70%, 40-75%, 50-60%, 50-70%, 50-75%, 60-70%, 60-75%, or 70-75% of an individual polymer.

An exemplary drug reservoir comprises or consists essentially of donepezil base generated in situ by reaction of donepezil HCl and sodium bicarbonate; a solvent composition comprising a hydrophilic solvent, permeation enhancer, and optionally one or both triethyl citrate and sorbitan monolaurate; a crosslinked polyvinylpyrrolidone and a copolymer of acrylic acid/vinyl acetate. In another exemplary drug reservoir, a composition that comprises or consisting essentially of donepezil base generated in situ by reaction of between about 5-25 wt % or 10-25 wt % donepezil HCl and between about 1-5 wt % sodium bicarbonate; about 0-15 wt % or 5-15 wt % triethyl citrate; about 0-5 wt % or 0.5-5 wt % sorbitan monolaurate; about 5-15 wt % glycerin; about 1-10 wt % lauryl lactate; about 5-25 wt % crosslinked polyvinylpyrrolidone; and about 30-65 wt % or 30-50 wt % acrylate-vinylacetate copolymer is contemplated. In another example, a composition consisting essentially of donepezil base generated in situ by reaction of between about 10-18 wt % or 14-18 wt % donepezil HCl and between about 1-5 wt % or 2-5 wt % sodium bicarbonate; about 8-12 wt % triethyl citrate; about 1.5-2.5 wt % sorbitan monolaurate; about 9-11 wt % glycerin; about 1-10 wt % lauryl lactate; about 13-17 wt % crosslinked polyvinylpyrrolidone; and about 40-42 wt % acrylate-vinylacetate copolymer is contemplated. The permeation enhancer lauryl lactate can be between about 0.5-10 wt %, 0.5-7.5 wt %, 1-10 wt %, 1-7 wt %, 1-5 wt %, 2-7 wt %, 2-5 wt %, or 1.5-5 wt % or 1.5-4 wt %.

A drug reservoir as described herein and hereinabove is contemplated for use in a transdermal delivery system, where the system additionally comprises a skin contact adhesive. The skin contact adhesive layer may be fabricated from any of the adhesive materials listed herein and hereinabove. The skin contact adhesive layer, in one embodiment comprises between about 50-90 wt % of adhesive polymer or copolymer, or between about 55-90 wt %, or between about 60-90 wt %, between about 65-90 wt %, between about 70-90 wt %, between about 75-90 wt %, or between about 80-90 wt %. In one embodiment, the skin contact adhesive is comprised of a copolymer of acrylic acid/vinyl acetate. In another embodiment, the skin contact adhesive layer additionally comprises a polyvinylpyrrolidone, such as a crosslinked polyvinylpyrrolidone.

The skin contact adhesive layer may also comprise a solvent mixture that may comprise a permeation enhancer. In embodiments, the skin contact adhesive layer comprises a solvent composition that comprises a permeation enhancer and one or both of triethyl citrate and sorbitan monolaurate. In one embodiment, the skin contact adhesive layer as manufactured does not include a pharmaceutically active agent intended for systemic delivery—for example, the ingredients combined to form the skin contact adhesive layer do not include donepezil base or a donepezil salt. However, the skin contact adhesive layer when fabricated into a transdermal delivery system and stored for a period of time and/or during use will contain the pharmaceutically active agent intended for systemic delivery because the agent will diffuse from the drug reservoir adhesive matrix into the skin contact adhesive layer.

The penetration or permeation enhancer in either or both of the skin contact adhesive layer and the drug reservoir may be chosen from a wide range of such compounds known in the art. In some embodiments, permeation enhancers for use in the adhesive matrix include, but are not limited to, methyl laurate, propylene glycol monolaurate, glycerol monolaurate, glycerol monooleate, lauryl lactate, myristyl lactate, and dodecyl acetate. Additional permeation enhancers are described in U.S. Pat. No. 8,874,879, which is incorporated herein by reference. It will be appreciated that the compositions herein may include one or more or at least one permeation enhancer. In embodiments, the penetrating or permeating enhancer is included in an amount between about 1-10%, about 2-5%, about 2-10% relative to the weight of the adhesive matrix (inclusive of sub-ranges). In other embodiments, the permeation enhancer is present in the drug reservoir and/or the contact adhesive layer in an amount between about 0.5-10 wt %, 0.5-7.5 wt %, 1-7 wt %, 1-5 wt %, 2-7 wt %, 2-5 wt %, or 1.5-5 wt % or 1.5-4 wt %.

Either or both of the skin contact adhesive layer and the drug reservoir may further include one or more matrix modifiers. Without wishing to be bound by theory, it is believed that the matrix modifier facilitates homogenization of the adhesive matrix. Sorption of hydrophilic moieties is a possible mechanism for this process. Thus, known matrix modifiers which are to some degree water-sorbent may be used. For example, possible matrix modifiers include colloidal silicone dioxide, fumed silica, cross-linked polyvinylpyrrolidone (PVP), soluble PVP, cellulose derivatives (e.g. hydroxypropyl cellulose (HPC), hydroxyethylcellulose (HEC)), polyacrylamide, polyacrylic acid, a polyacrylic acid salt, or a clay such as kaolin or bentonite. An exemplary commercial fumed silica product is Cab-O-Sil (Cabot Corporation, Boston, Mass.). The hydrophilic mixtures described in U.S. Published Patent Application No. 2003/0170308 may also be employed, for example mixtures of PVP and PEG or of PVP, PEG, and a water-swellable polymer such as the polymethacrylate-based copolymers sold under the trade name EUDRAGIT, and in particular EUDRAGIT® L100-55.

In embodiments, the matrix modifier is individually included in the contact adhesive layer in an amount between about 1-40%, about 10-30%, about 15-25%, about 5-7%, about 7-20%, or about 7-25% relative to the weight of the adhesive matrix (inclusive of sub-ranges), including, at least about 3%, e.g., about 4%, about 5%, about 6%, about 7%, about 8%, about 9%, about 10%, about 11%, about 12%, about 13%, about 14%, about 15%, about 16%, about 17%, about 18%, about 19%, about 20%, or greater % by weight, wherein all values are relative to the weight of the entire adhesive layer. In some embodiments, the matrix modifier does not include ethylcellulose.

Either or both of the skin contact adhesive layer and the drug reservoir may further include other conventional additives such as adhesive agents, antioxidants, crosslinking or curing agents, pH regulators, pigments, dyes, refractive particles, conductive species, antimicrobial agents, opacifiers, gelling agents, viscosity modifiers or thickening agents, stabilizing agents, and the like as known in the art. In those embodiments wherein adhesion needs to be reduced or eliminated, conventional detackifying agents may also be used. Other agents may also be added, such as antimicrobial agents, to prevent spoilage upon storage, i.e., to inhibit growth of microbes such as yeasts and molds. Suitable antimicrobial agents are typically selected from the group consisting of the methyl and propyl esters of p-hydroxybenzoic acid (i.e., methyl and propyl paraben), sodium benzoate, sorbic acid, imidurea, and combinations thereof. These additives, and amounts thereof, are selected in such a way that they do not significantly interfere with the desired chemical and physical properties of the adhesive and/or active agent.

Either or both of the skin contact adhesive layer and the drug reservoir may further may also contain irritation-mitigating additives to minimize or eliminate the possibility of skin irritation and/or skin damage resulting from the drug, the enhancer, or other components of the composition. Suitable irritation-mitigating additives include, for example: α-tocopherol; monoamine oxidase inhibitors, particularly phenyl alcohols such as 2-phenyl-1-ethanol; glycerin; salicylic acids and salicylates; ascorbic acids and ascorbates; ionophores such as monensin; amphiphilic amines; ammonium chloride; N-acetylcysteine; cis-urocanic acid; capsaicin; chloroquine; and corticosteriods.

Figure 1B:
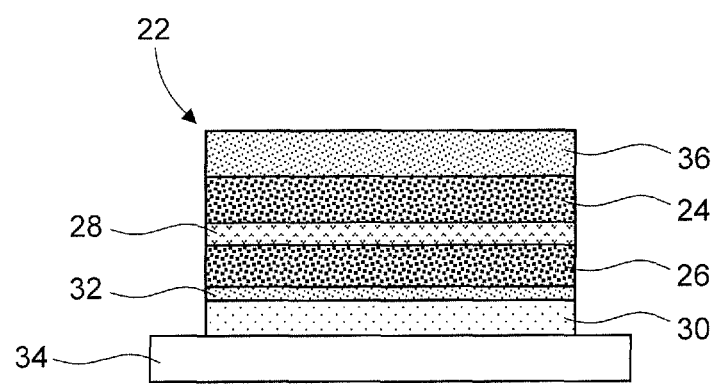
Figure 1C:
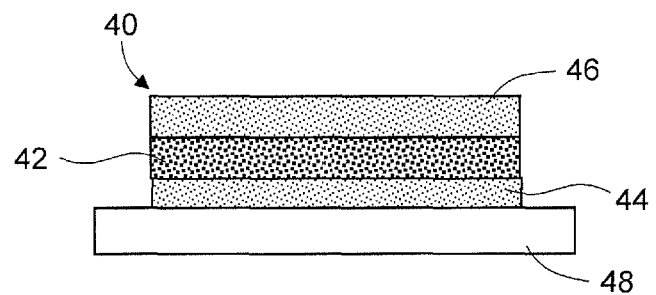

A transdermal delivery system comprised of a drug reservoir and a skin contact adhesive can have a variety of configurations, and several non-limiting examples are depicted in are set forth in FIGS. 1A-1D. FIG. 1A illustrates a transdermal delivery system 10 comprised of a drug reservoir 12 and a contact adhesive 14 separated by a rate controlling membrane or by a non-rate controlling material, such as a tie layer composed of a non-woven polyester or polypropylene, 16. A backing layer 18 and a release liner 20 are also present. FIG. 1B illustrates a second embodiment of a transdermal delivery system 22 comprised of a first drug reservoir 24 and a second drug reservoir 26, the first and second drug reservoirs separated by a non-rate controlling material, such as a tie layer composed of a non-woven polyester or polypropylene, 28. A contact adhesive layer 30 provides for attachment of the system to the skin of a user, where a rate controlling membrane 32 controls release of therapeutic agent from the second drug reservoir into the contact adhesive and ultimately onto the skin of a user. A release liner 34 and a backing layer 36 are also present. FIG. 1C shows another embodiment of a transdermal delivery system 40 comprised of a drug reservoir 42 and a contact adhesive layer 44 that provides for attachment of the system to the skin of a user. A backing layer 46 and a release liner 48 are also present.

Figure 1D:
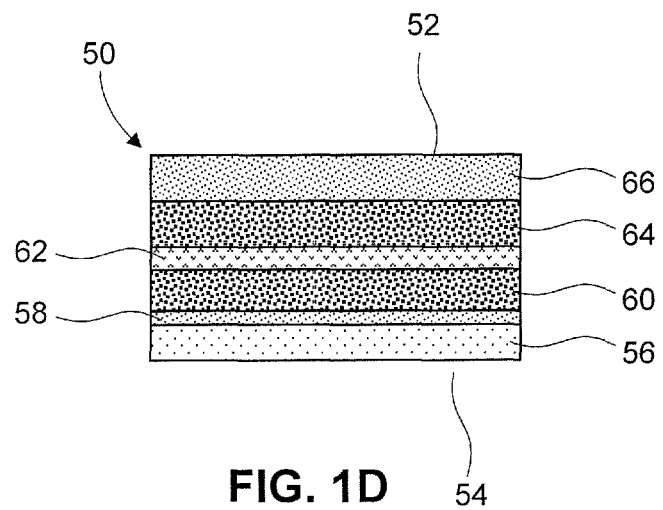

FIG. 1D shows another embodiment of a transdermal delivery system for systemic delivery of donepezil base. The system 50 comprises, in series from the skin facing side 52 to the external environment facing side 54, a skin contact adhesive layer 56 to attach the system to the skin of a user. In one embodiment, the skin contact adhesive layer manufactured is manufactured from an adhesive formulation that does not comprise donepezil base or a donepezil salt. Directly in contact with the skin contact adhesive layer is an intermediate layer 58. The intermediate layer can be, for example, a non-woven polyester material or a drug rate-controlling membrane, such as a microporous polyethylene or polyprolylene. The intermediate layer has opposing sides, a skin-facing side (that is in contact with the skin contact adhesive layer 56) and an environment facing side. On the environment facing side of the intermediate layer is a drug reservoir 60. The drug reservoir comprises donepezil HCl and an alkaline salt. These components react in situ to generate donepezil base in the drug reservoir that is delivered to the user after application of the system to the skin. In contact with the drug reservoir layer is a first backing layer 62, and in contact with the first backing layer is an optional adhesive overlay 64. An optional second backing layer 66 is in contact with the adhesive overlay and with the environment. In one embodiment, the optional adhesive overlay 64 is composed of two different adhesive layers—for example a first layer of polyisobutylene and polybutene, with or without a crosslinked polyvinylpyrrolidone, and a second layer of an acrylic adhesive. In another embodiment, the optional adhesive overlay 64 is composed of a single layer of an acrylate adhesive.

Accordingly, in one embodiment a transdermal delivery system for systemic delivery of donepezil base is provided. The system comprises, in series from the skin facing side to the external environment, a skin contact adhesive layer to attach the system to the skin of a user, the skin contact adhesive layer optionally manufactured from an adhesive formulation that does not comprise donepezil base or a donepezil salt. Directly in contact with the skin contact adhesive layer is an intermediate layer. On the opposing surface of the intermediate layer is a drug reservoir comprised of a solvent composition and donepezil base generated in situ by reaction of donepezil HCl and an alkaline salt. In one embodiment, the solvent composition comprises one or more of triethyl citrate, a surfactant, a permeation enhancer. In a preferred embodiment, the solvent composition comprises triethyl citrate, a surfactant, an α-hydroxy acid permeation enhancer. The drug reservoir, in one embodiment, comprises an adhesive that can be a copolymer of acrylic acid/vinyl acetate.

The intermediate layer, also referred to as a fabric layer, a membrane or a tie layer, may be formed of any suitable material including, but not limited to, polyesters, vinyl acetate polymers and copolymers, polyethylenes, and combinations thereof. In one embodiment, the intermediate layer is a nonwoven layer of polyester fibers such as the film sold under the name Reemay® (Kavon Filter Products Co.). In embodiments, the intermediate layer does not affect the rate of release of the active agent from the adhesive layers. In another embodiment, the intermediate layer is a rate controlling membrane for donepezil base.

In one embodiment, the intermediate layer is a microporous membrane comprising a plurality of pores. In exemplary transdermal systems prepared as described in the working examples, the plurality of pores in the microporous membrane contains a solvent composition. In one embodiment, the solvent composition in the pores of the microporous membrane is comprised of one or more of the solvents present in either or both of the drug reservoir and the contact adhesive. For example, an exemplary solvent composition contained in the pores of the microporous membrane is one or more of triethyl citrate, a surfactant, an α-hydroxy acid permeation enhancer. Another exemplary embodiment is a solvent composition comprised of one or more of triethyl citrate, sorbitan monolaurate, and lauryl lactate. In one embodiment, the solvent composition comprises between 40-80 wt % triethyl citrate, between 5-40 wt % lauryl lactate and between 5-25 wt % sorbitan laurate. In another embodiment, the solvent composition comprises between 50-75 wt % or 55-70 wt % triethyl citrate, between 10-35 wt % or 15-30 wt % lauryl lactate and between 8-20 wt % or between 10-15 wt % sorbitan laurate. In one embodiment, the solvent composition contained in the pores of the microporous membrane excludes the hydrophilic solvent present in the drug reservoir. In one embodiment, the solvent composition contained in the pores of the microporous membrane excludes glycerin.

The microporous membrane may be pretreated with the solvent composition so that its pores are saturated with, filled with, or partially filled with the solvent composition. The microporous membrane is, in one embodiment, a polypropylene microporous membrane and may have an average pore size in the range of about 0.001 μm to about 100 μm, about 1 μm to about 10 m, about 0.010 μm to about 0.100 μm, or about 0.040 μm to about 0.050 μm. For example, the average pore size can be about 0.035 μm, 0.036 μm, 0.037 μm, 0.038 μm, 0.039 μm, 0.040 μm, 0.041 μm, 0.042 μm, 0.043 μm, 0.044 μm, 0.045 μm, 0.046 μm, 0.047 μm, 0.048 μm, 0.049 μm, or 0.050 μm. In some embodiments, the microporous membrane has an average pore size of about 0.043 μm. The microporous membrane is, in one embodiment, a polypropylene microporous membrane and has a porosity in the range of about 30% to about 50%, about 35% to about 45%, or about 40% to about 42%. For example, the microporous membrane can have a porosity of about 30%, 31%, 32%, 33%, 34%, 35%, 36%, 37%, 38%, 39%, 40%, 41%, 42%, 43%, 44%, 45%, 46%, 47%, 48%, 49%, or 50%.

The adhesive overlay in the delivery system of FIG. 1D is comprised, in one embodiment, of a polyisobutylene and polybutene mixture. In another embodiment, the adhesive overlayer is comprised of a first layer and a second layer, the first layer composed of a polyisobutylene, polybutene and crosslinked polyvinylpyrrolidone mixture and the second layer composed of an acrylic adhesive. Polyisobutylene is a vinyl polymer comprised of the isobutylene monomer. Polybutene is a viscous, non-drying, liquid polymer, prepared by copolymerization of 1- and 2-butene with a small quantity of isobutylene. In some embodiments, the polybutene in one embodiment has a molecular weight of between about 750-6000 Daltons, preferably between about 900-4000 Daltons, and preferably between about 900-3000 Daltons. In some embodiments the mixture comprises polybutene in the polyisobutylene blend at about 40 weight percent. More generally, the polybutene is present in the polyisobutylene blend in an amount between 20-50 weight percent, or between 25-45 weight percent. In another embodiment, the adhesive overlayer is a single layer and comprised of an acrylate copolymer that forms the single layer adhesive overlay. An exemplary acrylate copolymer is DuroTak® 387-2052.

The transdermal delivery system comprises a backing layer that provides a structural element for holding or supporting the underlying adhesive layer(s). The backing layer may be formed of any suitable material as known in the art. In some embodiments, the backing layer is occlusive. In some embodiments, the backing is preferably impermeable or substantially impermeable to moisture. In one exemplary embodiment, the barrier layer has a moisture vapor transmission rate of less than about 50 g/m²-day. In some embodiments, the backing layer is preferably inert and/or does not absorb components of the adhesive layer, including the active agent. In some embodiments, the backing layer preferably prevents release of components of the adhesive layer through the backing layer. The backing layer may be flexible or nonflexible. The backing layer is preferably at least partially flexible such that the backing layer is able to conform at least partially to the shape of the skin where the patch is applied. In some embodiments, the backing layer is flexible such that the backing layer conforms to the shape of the skin where the patch is applied. In some embodiments, the backing layer is sufficiently flexible to maintain contact at the application site with movement, e.g. skin movement. Typically, the material used for the backing layer should permit the device to follow the contours of the skin or other application site and be worn comfortably on areas of skin such as at joints or other points of flexure, that are normally subjected to mechanical strain with little or no likelihood of the device disengaging from the skin due to differences in the flexibility or resiliency of the skin and the device.

In some embodiments, the backing layer is formed of one or more of a film, non-woven fabric, woven fabric, laminate, and combinations thereof. In some embodiments, the film is a polymer film comprised of one or more polymers. Suitable polymers are known in the art and include elastomers, polyesters, polyethylene, polypropylene, polyurethanes and polyether amides. In some embodiments, the backing layer is formed of one or more of polyethylene terephthalate, various nylons, polypropylene, metalized polyester films, polyvinylidene chloride, and aluminum foil. In some embodiments, the backing layer is a fabric formed of one or more of polyesters such as polyethylene terephthalate, polyurethane, polyvinyl acetate, polyvinylidene chloride and polyethylene. In one particular, but non-limiting embodiment, the backing layer is formed of a polyester film laminate. One particular polyester film laminate is the polyethylene and polyester laminate such as the laminate sold under the name SCOTCHPAK™ #9723.

In embodiments, the device includes a release liner at least partially in contact at least with the adhesive layer to protect the adhesive layer prior to application. The release liner is typically a disposable layer that is removed prior to application of the device to the treatment site. In some embodiments, the release liner preferably does not absorb components of the adhesive layer, including the active agent. In some embodiments, the release liner preferably impermeable to components of the adhesive layer (including the active agent) and prevents release of components of the adhesive layer through the release liner. In some embodiments, the release liner is formed of one or more of a film, non-woven fabric, woven fabric, laminate, and combinations thereof. In some embodiments, the release liner is a silicone-coated polymer film or paper. In some non-limiting embodiments, the release liner is a silicone-coated polyethylene terephthalate (PET) film, a fluorocarbon film, or a fluorocarbon coated PET film.

The thickness and/or size of the device and/or adhesive matrices may be determined by one skilled in the art based at least on considerations of wearability and/or required dose. It will be appreciated that the administration site for the device will affect the wearability considerations due to the available size of the administration site and the use of the administration site (e.g. need for flexibility to support movement). In some embodiments, the device and/or adhesive matrix has a thickness of between about 25-500 µm. In some embodiments, the device and/or adhesive matrix has a thickness of between about 50-500 µm. In some embodiments, the patch has a size in the range of about 16 $cm^2$-225 $cm^2$. It will be appreciated that the thickness and size provided here are merely exemplary and the actual thickness and or size may be thinner/smaller or thicker/larger as needed for a specific formulation.

Fabrication of a transdermal delivery system is routinely done by skilled artisans and involves casting or extruding each of the adhesive layers onto a suitable film such as a release liner or onto another layer of the transdermal delivery system, and drying if needed to remove solvents and/or volatile compounds. Layers of the transdermal delivery system can be laminated together to form the final system.

Transdermal delivery systems and drug reservoir adhesive matrices were prepared to illustrate the embodiments described herein. Examples 1-3 set forth exemplary compositions and delivery systems. As described in Example 1, a transdermal delivery system comprised a drug reservoir and a contact adhesive with a rate controlling membrane situated between the drug reservoir and the contact adhesive, as depicted in FIG. 1A. A drug reservoir in the form of a solid monolithic adhesive reservoir was prepared using an acrylic acid/vinyl acetate copolymer adhesive with a solvent mixture that included a permeation enhancer. In one embodiment, the solvent mixture is comprised of triethyl citrate, lauryl lactate and sorbitan monolaurate. The drug reservoir contained approximately 5 wt % donepezil hydrochloride and sodium bicarbonate, to generate in situ donepezil base. A contact adhesive layer comprised of the same acrylic acid/vinyl acetate copolymer adhesive, along with triethyl citrate, lauryl lactate and ethyl acetate was prepared. A rate controlling membrane, to control the diffusional release of donepezil base from the drug reservoir, separated the drug reservoir and the contact adhesive.

As described in Examples 2 and 3, transdermal delivery systems were prepared and were comprised of an adhesive matrix drug reservoir and a skin contact adhesive layer separated by an intermediate layer. The adhesive matrix drug reservoir in the exemplary systems comprised the adhesive copolymer acrylic acid/vinyl acetate and in one example additionally included a cross-linked polyvinylpyrrolidone (Example 2). The acrylic acid/vinyl acetate was added to a solvent mixture that comprised a permeation enhancer (the solvent mixture in this embodiment was triethyl citrate, sorbitan monolaurate, lauryl lactate, and glycerin), donepezil hydrochloride and sodium bicarbonate. The skin contact adhesive layer was comprised of sorbitan monolaurate, triethyl citrate, and lauryl lactate, along with acrylic acid/vinyl acetate copolymer. In these exemplary delivery systems, a microporous membrane to control the rate of release of donepezil base from the adhesive matrix drug reservoir was laminated to one side of the rate controlling membrane was situated between the adhesive matrix drug reservoir and the skin contact adhesive. A release liner and a backing member were laminated to form a final delivery system.

Accordingly, in one embodiment, a composition comprising an adhesive matrix comprising or consisting essentially of donepezil base generated in situ by reaction of donepezil HCl and sodium bicarbonate; a solvent composition comprised of triethyl citrate, sorbitan monolaurate, and glycerin; and a polymeric, adhesive matrix of crosslinked polyvinylpyrrolidone and a copolymer of acrylic acid/vinyl acetate is provided. In another embodiment, a composition, comprising an adhesive matrix comprising or consisting essentially of donepezil base generated in situ by reaction of between about 10-25 wt % donepezil HCl and between about 1-5 wt % sodium bicarbonate; about 5-15 wt % triethyl citrate; about 0.5-5 wt % sorbitan monolaurate; about 5-15 wt % glycerin; about 5-25 wt % crosslinked polyvinylpyrrolidone; and about 30-50 wt % acrylate-vinylacetate copolymer is provided. In another embodiment, composition comprising an adhesive matrix comprising or consisting essentially of donepezil base generated in situ by reaction of between about 14-18 wt % donepezil HCl and between about 2-5 wt % sodium bicarbonate; about 8-12 wt % triethyl citrate; about 1.5-2.5 wt % sorbitan monolaurate; about 9-11 wt % glycerin; about 13-17 wt % crosslinked polyvinylpyrrolidone; and about 40-42 wt % acrylate-vinylacetate copolymer is provided.

The compositions described are intended for use in a transdermal delivery system for systemic delivery of donepezil. The adhesive compositions are manufactured using a salt form of donepezil and a weak base (alkaline salt), to generate in situ the base form of donepezil that is delivered via the skin for systemic uptake. The transdermal delivery system also comprises one or more of triethyl citrate, lauryl lactate, glycerin, sorbitan laurate, and ethyl acetate in the drug reservoir, and one or more of triethyl citrate, lauryl lactate, sorbitan laurate, and ethyl acetate in the skin contact adhesive. In one embodiment, the drug reservoir and the contact adhesive each comprise one or more of triethyl citrate, lauryl lactate and sorbitan laurate. In one embodiment, the skin contact adhesive does not comprise glycerin. In another embodiment, the transdermal system comprises a microporous membrane with a plurality of pores that contain, are filled or partially filled, or saturated with one or more of the same solvents in one or both of the drug reservoir and the contact adhesive. In one embodiment, the plurality of pores in the microporous membrane comprise a solvent composition that comprises one or more of triethyl citrate, lauryl lactate and sorbitan laurate. The triethyl citrate may be present in the drug reservoir, the pores of the microporous membrane, and/or the contact adhesive in an amount between about 1-20 wt %, 2-25 wt %, 5-15 wt %, 5-12 wt %, 7-15 wt %, 7-12 wt %, 8-12 wt %, 9-12 wt %, 1-8 wt %, 1-6 wt %, 1-5 wt %, 1.5-5 wt %, 2-5 wt % or 2.5-5 wt % or 2.5-4.5 wt %. Ethyl acetate may be present in the drug reservoir, the pores of the microporous membrane, and/or the contact adhesive in an amount between about 25-60 wt %, where in one embodiment, a greater amount of ethyl acetate is present in the drug reservoir than in the contact adhesive, where the drug reservoir comprises 1.2, 1.3, 1.4, 1.5, 1.6, 1.7 or 1.8 times more ethyl acetate than the contact adhesive layer. Sorbitan laurate may be present in the drug reservoir, the pores of the microporous membrane, and/or the contact adhesive in an amount between about 0.01-5 wt % or 0.1-5 wt %, where in one embodiment, sorbitan laurate is present in the drug reservoir and in the contact adhesive in the same amounts (on a w/w basis of the total amount in each layer individually, e.g., the amount in weight percent in the drug reservoir layer is the same as the amount in weight percent in the contact adhesive layer). In another embodiment, the drug reservoir, the pores of the microporous membrane, and/or the contact adhesive comprise lauryl lactate in an amount between about 0.1-10 wt %, 0.5-8 wt % or 0.5-7 wt %, 1-7 wt %, 1-5 wt %, 1.5-5 wt %, 2-5 wt %, 2.5-5 wt %, 0.25-5 wt %, 0.5-5 wt % or 0.5-4 wt %, 0.5-4.5 wt %. In one embodiment, the drug reservoir comprises an amount of lauryl lactate that is equal to or within about 0.5%, 1%, 5 wt %, 10 wt %, 15 wt % or 20 wt % of the amount of lauryl lactate present in the contact adhesive layer.

III. Method of Treatment

Based on the exemplary compositions and transdermal delivery systems (also referred to as transdermal devices or devices) described herein, a method for treating a suitable condition with donepezil is provided. In embodiments, compositions and devices comprising donepezil are useful for treating, delaying progression, delaying onset, slowing progression, preventing, providing remission, and improvement in symptoms of cognitive disorders or disease are provided herein. In embodiments, compositions and devices comprising donepezil are provided for maintaining mental function including, but not limited to a least one of maintaining thinking, memory, speaking skills as well as managing or moderating one or more behavioral symptoms of a cognitive disorder or disease. In embodiments, the cognitive disorder is Alzheimer's disease. In particular embodiments, the cognitive disorder is Alzheimer's type dementia. In embodiments, compositions and devices comprising donepezil are provided for use in treating, etc. mild, moderate, or severe Alzheimer's disease.

Alzheimer's disease is the most common cause of senile dementia and is characterized by cognitive deficits related to degeneration of cholinergic neurons. Alzheimer's affects 6-8% of people over the age of 65 and nearly 30% of people over the age of 85 (Sozio et al., *Neurophsychiatric Disease and Treatment*, 2012, 8:361-368), involving the loss of cognitive functioning and behavioral abilities. The causes of Alzheimer's disease are not yet fully understood. As Alzheimer's disease is associated with reduced levels of several cerebral neurotransmitters including acetylcholine (Ach), current treatment includes administering cholinesterase inhibitors. Cholinesterase inhibitors reduce the hydrolysis of acetylcholine in the synaptic cleft by inhibiting cholinesterase and/or butyrylcholinesterase, which increases acetylcholine levels resulting in improved neurotransmission (Id.).

The transdermal devices described herein may be designed for long term use and/or continuous administration of the active agent. The FDA has approved daily oral doses of donepezil of 5 mg, 10 mg, and 23 mg. It will be appreciated that the total dose of the active agent per transdermal device will be determined by the size of the device and the loading of the active agent within the adhesive matrix. In an embodiment, the active agent is donepezil in free base form. Lower drug loading of donepezil base may be effective as compared to the salt form (e.g. donepezil hydrochloride). The ability to include lower drug loading to achieve efficacy results in a lower profile for the device (thinner) and/or smaller size, both of which are desirable to reduce discomfort. In some embodiments, the application period for the transdermal device is between about 1-10 days, 1-7 days, 1-5 days, 1-2 days, 3-10 days, 3-7 days, 3-5 days, 5-10 days, and 5-7 days inclusive. In some embodiments, the active agent is released from the adhesive matrix as a continuous and/or sustained release over the application period.

A method for delivering donepezil base transdermally to a subject is provided. In the method a transdermal delivery system is applied to the skin, and upon application of the transdermal delivery system to the skin of a subject, transdermal delivery of the donepezil base occurs, to provide a systemic blood concentration of the agent (or a metabolite) that at steady state is bioequivalent to administration of the therapeutic agent orally. As discussed below, bioequivalency is established by (a) a 90% confidence interval of the relative mean Cmax and AUC of the therapeutic agent administered from the transdermal delivery system and via oral delivery between 0.7-1.43 or between 0.80 and 1.25, or (b) a 90% confidence interval of the ratios for AUC and Cmax of the therapeutic agent administered from the transdermal delivery system and via oral delivery between 0.7-1.43 or between 0.80 and 1.25

Standard PK parameters routinely used to assess the behavior of a dosage form in vivo (in other words when administered to an animal or human subject) include $C_{max}$ (peak concentration of drug in blood plasma), $T_{max}$ (the time at which peak drug concentration is achieved) and AUC (the area under the plasma concentration vs time curve). Methods for determining and assessing these parameters are well known in the art. The desirable pharmacokinetic profile of the transdermal delivery systems described herein comprise but are not limited to: (1) a $C_{max}$ for transdermally delivered form of the donepezil when assayed in the plasma of a mammalian subject following administration, that is bioequivalent to the $C_{max}$ or an orally delivered or an intravenously delivered form of the drug, administered at the same dosage; and/or (2) an AUC for transdermally delivered form of donepezil when assayed in the plasma of a mammalian subject following administration, that is preferably bioequivalent to the AUC for an orally delivered or an intraveneously delivered form of the drug, administered at the same dosage; and/or (3) a $T_{max}$ for transdermally delivered form of donepezil when assayed in the plasma of a mammalian subject following administration, that is within about 80-125% of the $T_{max}$ for an orally delivered or an intraveneously delivered form of the drug, administered at the same dosage. Preferably the transdermal delivery system exhibits a PK profile having a combination of two or more of the features (1), (2) and (3) in the preceding sentence. Preferably the transdermal delivery system exhibits a PK profile having one or both of the features (1) and (2).

In the field of pharmaceutical development the term "bioequivalence" will be readily understood and appreciated by the person skilled in the art. Various regulatory authorities have strict criteria and tests for assessing whether or not two drug products are bioequivalent. These criteria and tests are commonly used throughout the pharmaceutical industry and the assessment of bioequivalence is recognized as a standard form of activity in drug development programs where the characteristics and performance of one product are being compared to those of another product. Indeed in seeking approval to market certain types of products (e.g. those evaluated under the FDA's "Abbreviated New Drug Application" procedure), it is a requirement that the follow-on product be shown to be bioequivalent to a reference product.

In one embodiment, the method encompasses providing and/or administering a transdermal delivery system comprising donepezil base to a subject in a fasted state is bioequivalent to administration of the agent (in base or salt form) orally or intravenously to a subject also in a fasted state, in particular as defined by $C_{max}$ and AUC guidelines given by the U.S. Food and Drug Administration and the corresponding European regulatory agency (EMEA). In another embodiment, the method encompasses providing and/or administering a transdermal delivery system comprising donepezil base to a subject in a fasted state is bioequivalent to administration of the agent (in base or salt form) orally or intravenously to a subject also in a non-fasted or fed state. Under U.S. FDA and Europe's EMEA guidelines, two products or methods are bioequivalent if the 90% Confidence Intervals (CI) for AUC and $C_{max}$ are between 0.80 to 1.25 ($T_{max}$ measurements are not relevant to bioequivalence for regulatory purposes). Europe's EMEA previously used a different standard, which required a 90% CI for AUC between 0.80 to 1.25 and a 90% CI for $C_{max}$ between 0.70 to 1.43. Methods for determining Cmax and AUC are well known in the art.

The transdermal delivery system prepared according to Example 1 was tested in vivo for systemic delivery of donepezil, as described in Example 4. In this in vivo study, six human subjects received treatment with a transdermal delivery system applied to their skin and worn for one week, and then removed. Another group of six human subjects were treated with orally administered donepezil (ARICPET®) at a dose of 5 mg taken on day one and on day 7 of the study. Blood samples were taken from the subjects and plasma concentrations of donepezil determined. The results are shown in FIGS. 2A-2B.

Figure 2A:
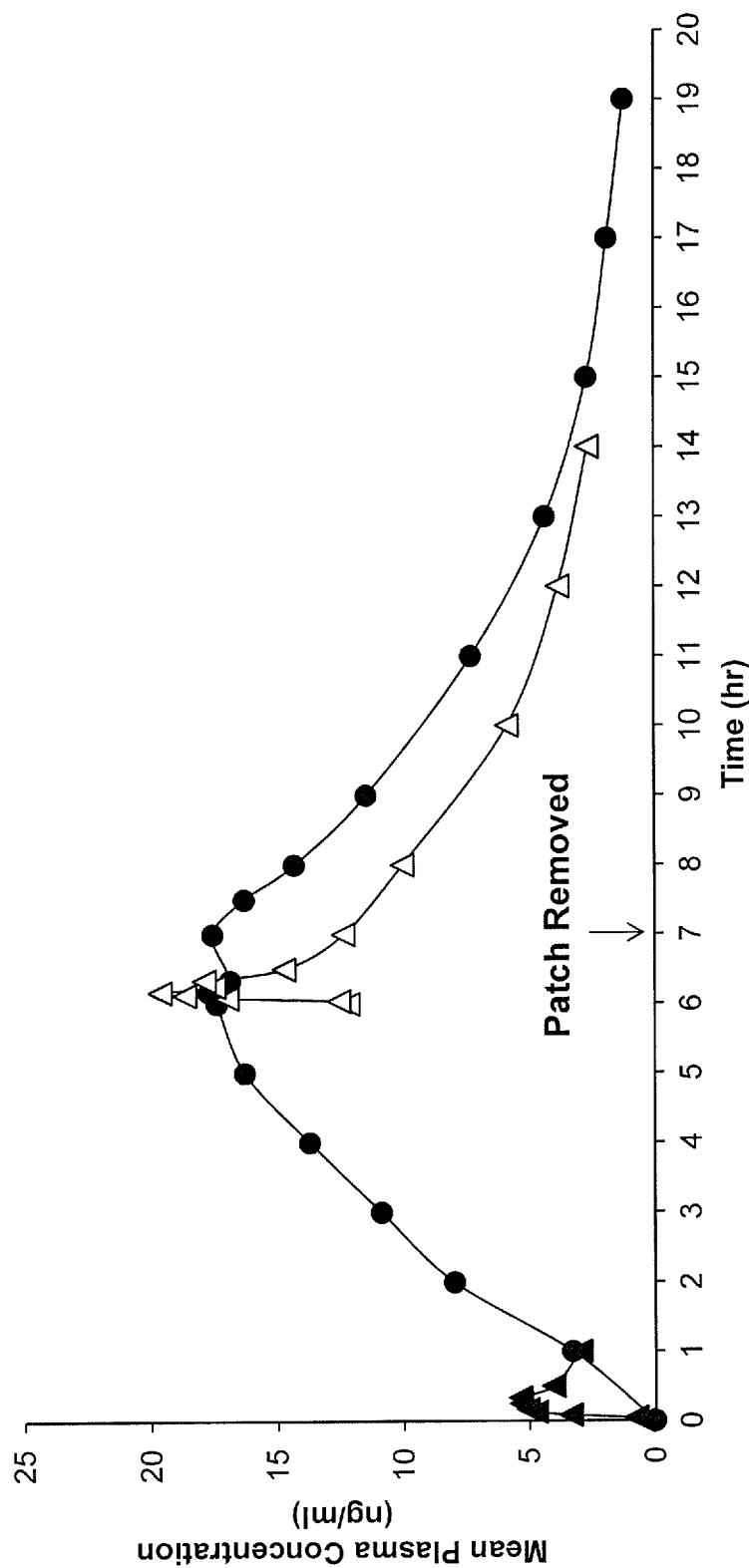
FIG. 2A is a graph of mean plasma concentration of donepezil, in ng/mL, as a function of time, in days, in human subjects treated with a donepezil transdermal delivery system (circles) for 1 week, or with 5 mg of donepezil administered orally on day 1 and on day 7 (triangles)

FIG. 2A shows the mean plasma concentration of donepezil, in ng/mL, in human subjects treated with a donepezil transdermal delivery system (circles) for 1 week, or with 5 mg of donepezil administered orally on day 1 and on day 7 (triangles). The donepezil transdermal delivery system provided a plasma concentration similar to the plasma concentration provided from oral delivery of a similar dose of donepezil. Accordingly, in one embodiment, a method of administering donepezil transdermally is provided by administering a transdermal delivery system that provides a pharmacokinetic profile that is bioequivalent to the pharmacokinetic profile obtained by oral administration of donepezil.

Figure 2B:
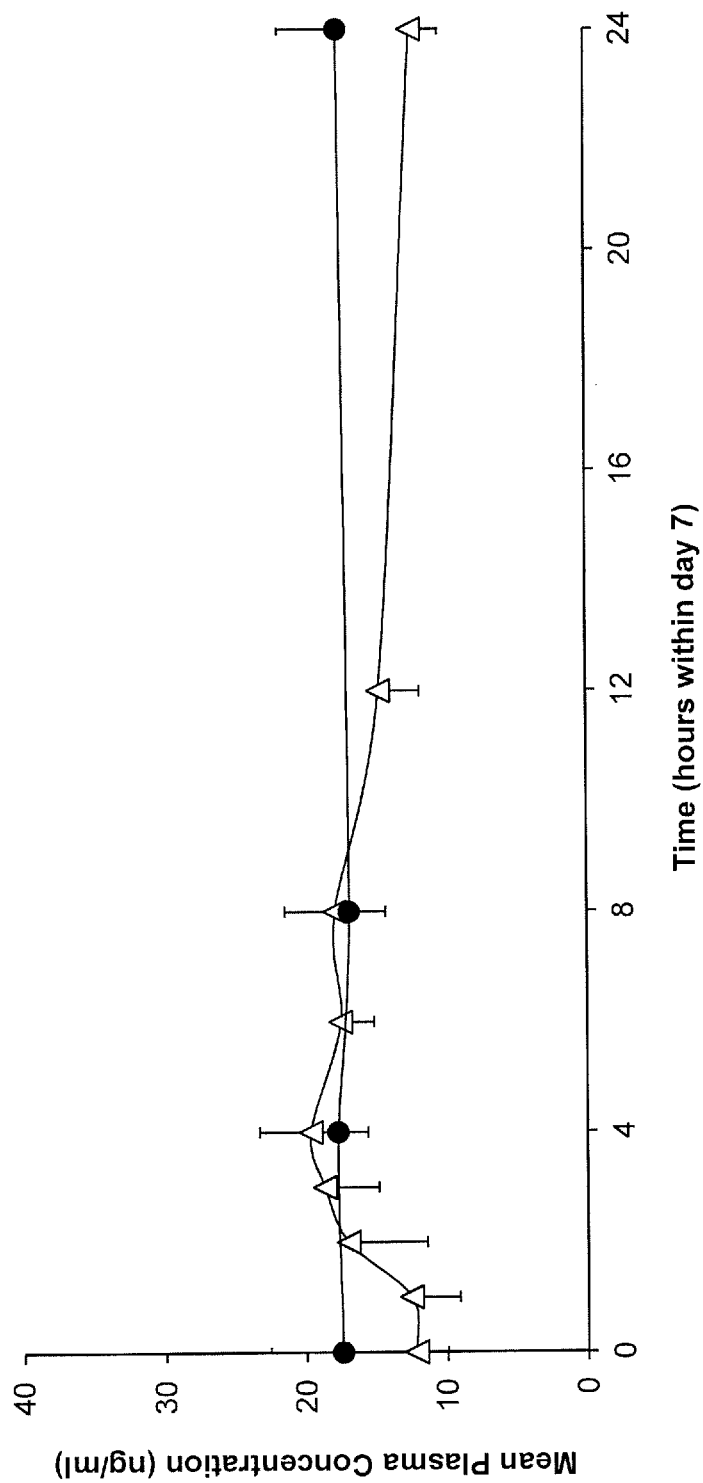
FIG. 2B is a graph showing the mean plasma concentration of donepezil, in ng/mL, in the 24 hour period after oral administration of a 5 mg donepezil tablet (triangles) and after removal of the donepezil transdermal delivery system (circles)

FIG. 2B is a graph showing a close up of the data points from FIG. 2A in the 24 hour period after oral administration of the 5 mg donepezil tablet (triangles) and after removal of the donepezil transdermal delivery system (circles). The transdermal delivery system provides a sustained, constant donepezil plasma concentration for 24 hours after its removal, similar to that observed in the 24 hour post oral administration.

Figure 3:
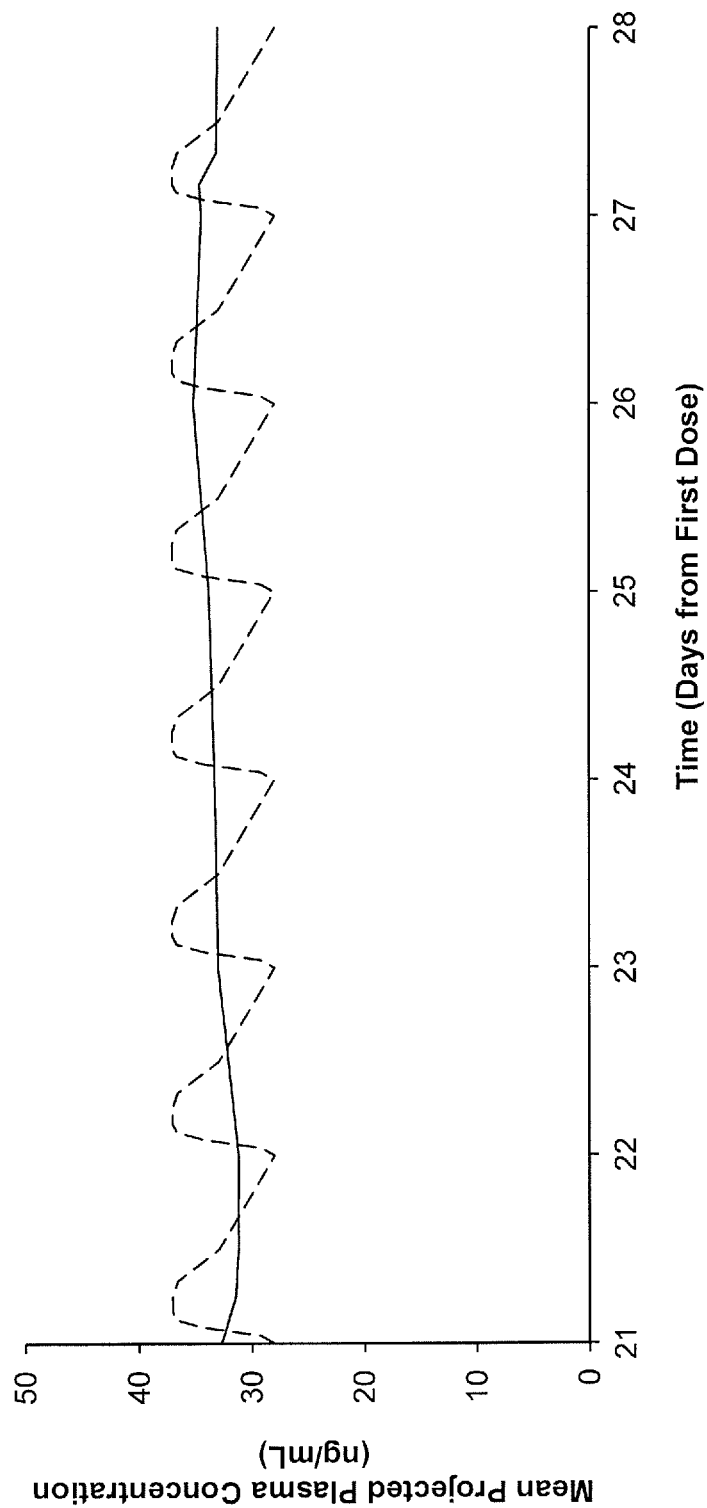
FIG. 3 is a graph showing the projected mean plasma concentration of donepezil, in ng/mL, in the last week of a 28 day (4 week) treatment period with a transdermal delivery system designed to administer 10 mg/day for a week (solid line), with a new patch applied once weekly, and over a 28 day period with a 10 mg daily oral tablet of donepezil (dashed line)

FIG. 3 is a graph showing the projected mean plasma concentration of donepezil, in ng/mL, in the last week of a 28 day (4 week) treatment period with a transdermal delivery system designed to administer 10 mg/day for a week (solid line) and over a 28 day period with a 10 mg daily oral tablet of donepezil (dashed line). The plasma fluctuations resulting from oral administration are eliminated by the transdermal system, where a fresh patch is applied each week and a constant plasma concentration is maintained over the treatment period. The transdermal delivery system provides a constant plasma concentration of donepezil for a sustained period of time (e.g., 3 days, 5 days, 7 days, 14 days), where the plasma concentration is essentially the same as or within about 10%, 15%, 20% or 30% of the plasma concentration achieved with daily oral administration of a similar daily dose of donepezil.

Figure 4:
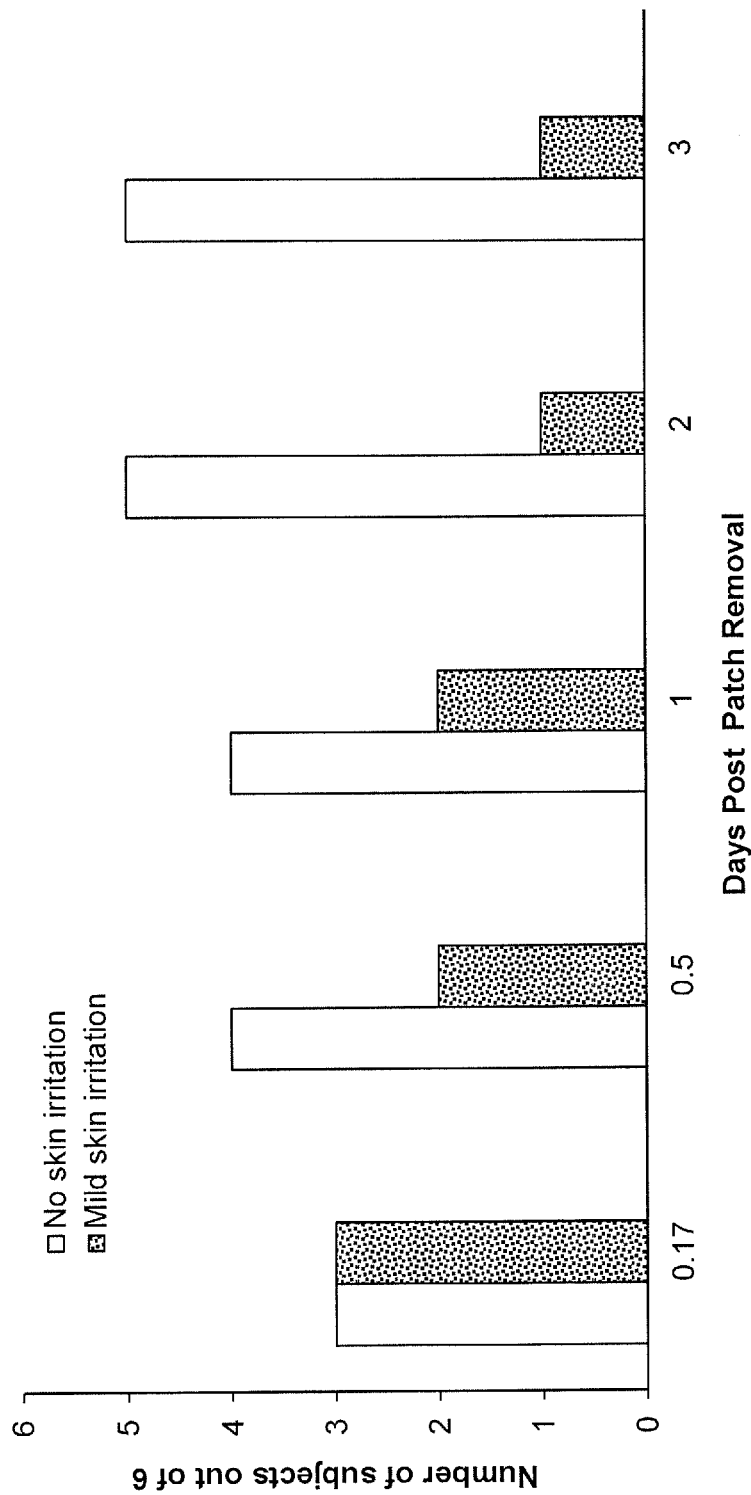
FIG. 4 is a bar graph of the number of subjects in the group treated with the donepezil transdermal delivery system for 1 week and the observed skin irritation subsequent to patch removal, where the open bars indicate no skin irritation and the filled bars indicate mild skin irritation.

With reference again to the study in Example 4, the six subjects treated with a donepezil transdermal delivery system for one week were monitored for several days following removal of the delivery system from their skin for signs of skin irritation. FIG. 4 is a bar graph showing the number of subjects out of the 6 in the group and the observed skin irritation in the period after removal of the delivery system, where the open bars indicate no skin irritation and the filled bars indicate mild skin irritation. The delivery system resulted in no or mild skin irritation in the hours after removal, and any mild irritation resolved with a day or two.

In another study, human subjects were treated with a transdermal delivery system designed to deliver systemically an amount of donepezil that is bioequivalent to orally administered donepezil at a 10 mg, once daily dose. The projected pharmacokinetic parameters Cmax, AUC and Cmin for the two routes of delivery are compared in Table 1.

TABLE 1

Projected Pharmacokinetic Parameters

| PK Parameter at Steady State | Once-weekly transdermal delivery system | 10 mg oral donepezil, once daily | Geometric Mean Ratio (transdermal:oral) |
|---|---|---|---|
| Geometric mean $C_{max}$ (ng/ml) | 40.6 | 45.6 | 0.890 |
| Geometric mean $C_{min}$ (ng/ml) | 34.2 | 30.8 | 1.110 |
| Geometric mean $AUC_{week}$ (ng-hr/ml) | 6367 | 6165* | 1.033 |

Accordingly, in one embodiment, a method for delivering donepezil base to a subject is provided. The method comprises providing a transdermal delivery system comprised of donepezil, and administering or instructing to administer the transdermal delivery system to the skin of a subject. The method achieves transdermal delivery of donepezil that is bioequivalent to administration of the therapeutic agent orally, wherein bioequivalency is established by (a) a 90% confidence interval of the relative mean Cmax and AUC of the therapeutic agent administered from the transdermal delivery system and via oral delivery between 0.70-1.43 or between 0.80 and 1.25, or (b) a 90% confidence interval of the geometric mean ratios for AUC and Cmax of the therapeutic agent administered from the transdermal delivery system and via oral delivery between 0.70-1.43 or between 0.80 and 1.25.

Figure 5A:
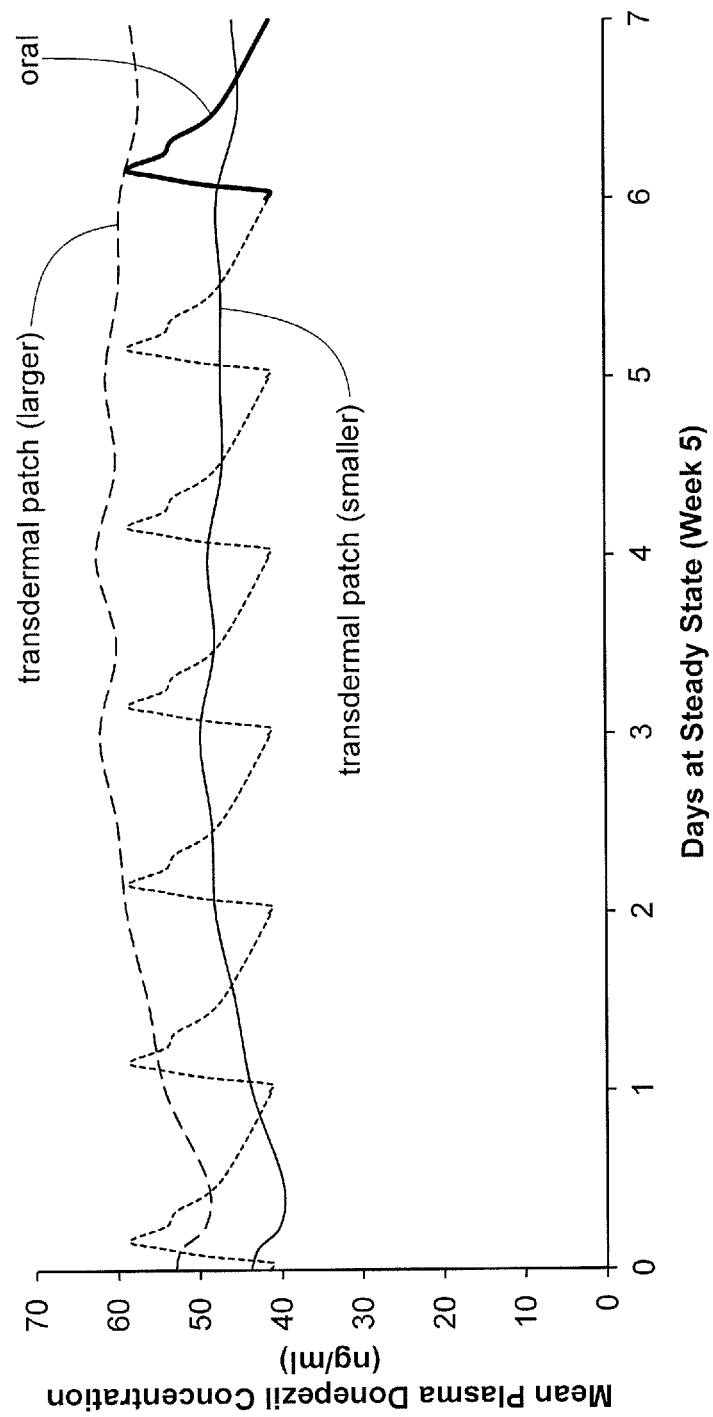
FIG. 5A shows the mean plasma concentration of donepezil, in ng/mL, at each day in week 5 of a clinical human study where subjects were treated with donepezil administered transdermally from transdermal patch with a first surface area (solid line) and a second, larger surface area (dashed line) and donepezil administered orally, where the donepezil plasma concentration for patients treated orally is indicated by the thick, bold line at days 6-7, and the dotted line shows the projected daily plasma concentration for oral treatment.

Example 5 describes a study conducted on human subjects where transdermal patches comprising donepezil were studied and compared to orally administered donepezil. In this study, patients were enrolled to participate in a six month, three-period, randomized crossover study comparing the steady-state pharmacokinetic profiles of once-daily oral donepezil (ARICEPT®) with a donepezil transdermal patch formulation. The transdermal patch was provided in two sizes, A and B, yet other than surface area, the transdermal patches were the same in all respects. During the study, the participants in each treatment arm received one week of 5 mg/day of donepezil, followed by 4 weeks of 10 mg/day of donepezil delivered from a once-weekly transdermal patch of two sizes (Arm 1 and Arm 2) or orally (Arm 3). Pharmacokinetic measurements were evaluated during the fourth week of the 10 mg/day treatment, when plasma concentrations had achieved steady levels. Blood samples for the subjects receiving the transdermal treatment were taken daily throughout the fourth week to determine pharmacokinetics. Subjects receiving oral donepezil had blood drawn on the last day of the fourth week to determine pharmacokinetics. The mean plasma concentration of donepezil, in ng/mL, is shown in FIG. 5A, for each day in week 5 of the study, where the solid line corresponds to the transdermal patch with a smaller surface area and the dashed line corresponds to the transdermal patch with a larger surface area. The thick, bold line at days 6-7 shows the mean plasma concentration for the subjects receiving the oral donepezil, and the dotted line shows the projected daily plasma concentration for oral treatment. The mean plasma concentrations of donepezil in the subjects treated with a transdermal patch were bioequivalent to the plasma concentration of donepezil in the subject treated orally with donepezil. The larger and smaller transdermal patches demonstrated dose proportionality. Table 2 shows the primary pharmacokinetic parameters in a bioequivalence assessment of the smaller surface area transdermal patch used in the study.

TABLE 2

| Primary Pharmacokinetic Parameter | Geometric Mean Ratio (%) of smaller patch to oral dose | Bioequivalence Limits (target 80-125%) |
|---|---|---|
| AUC (ng-hr/mL) | 104.7% | 95.2-115.2 |
| $Cmax_{ss}$ (ng/mL) | 91.6% | 83.1-100.8 |

Figure 5B:
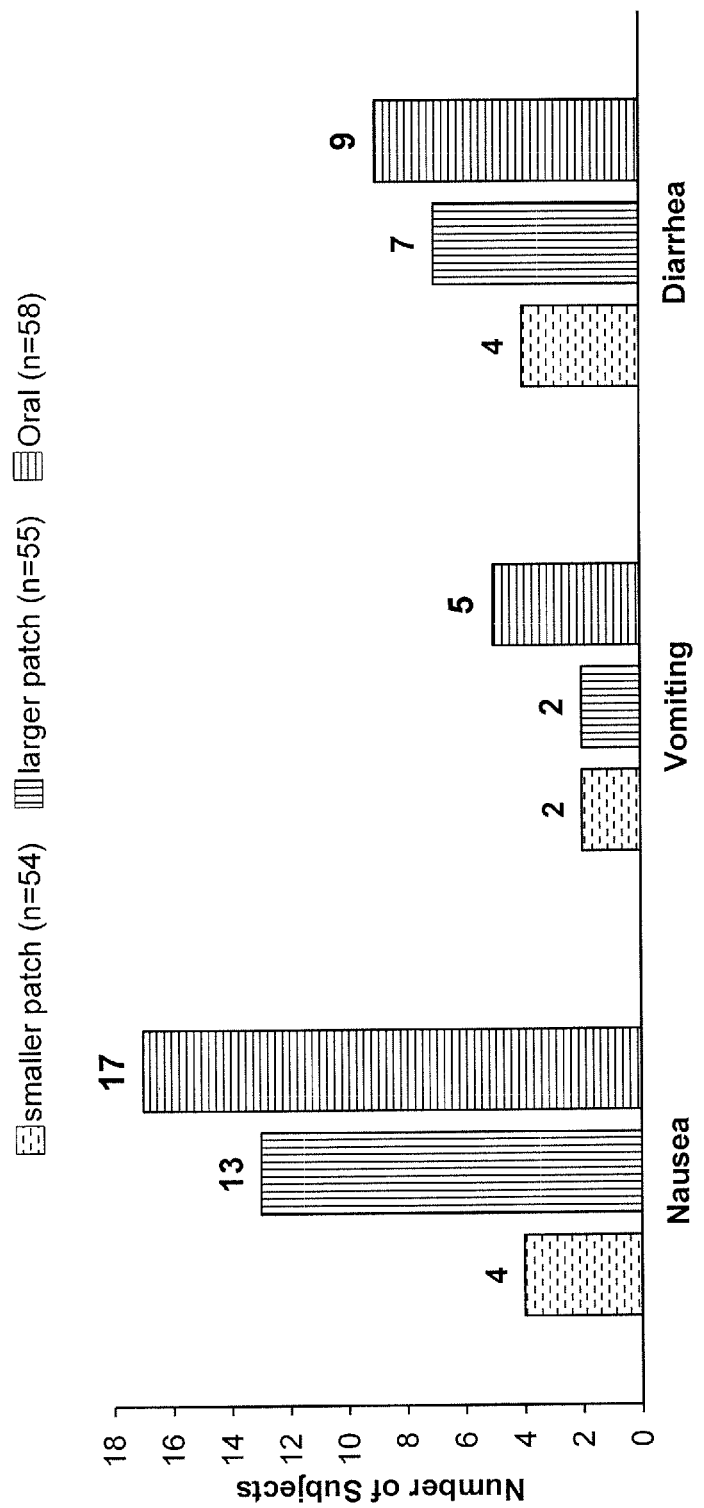
FIG. 5B is a bar graph showing the number of gastrointestinal related adverse events (nausea, vomiting and diarrhea) reported by subjects in a clinical study, where the subjects were treated as described in FIG. 5A; the bars with dashed fill correspond to subjects treated with the weekly smaller size transdermal patch, the bars with vertical line fill correspond to subjects treated with the weekly larger size transdermal patch, and the bars with horizontal line fill correspond to the subjects treated with oral donepezil.

The gastrointestinal related adverse events of nausea, vomiting and diarrhea reported by the subjects in the clinical study mentioned above with respect to FIG. 5A are shown in FIG. 5B. Subjects treated with the smaller size transdermal patch (bars with dashed fill) and with the larger size transdermal patch (bars with vertical line fill) had a lower incidence or nausea, vomiting and diarrhea than subjects treated with oral (bars with horizontal line fill) donepezil. The number of subjects experiencing nausea was four-fold lower when the 10 mg/day donepezil was administered transdermally versus orally. The number of subjects experiencing diarrhea was two-fold lower when 10 mg/day donepezil was administered transdermally versus orally.

Accordingly, in one embodiment, a composition and a method for delivering donepezil to a subject is provided. The composition, when applied to the skin of a subject, provides transdermal delivery of donepezil to achieve a plasma concentration of donepezil that at steady state is bioequivalent to administration of donepezil orally, and/or that provides a number of gastrointestinal related adverse events that is two-fold, three-fold, four-fold, or five-fold lower than subjects treated with the same dose of donepezil orally (i.e., the dose given orally is equal to the dose given transdermally, such that the subjects are treated with an equal dose of donepezil given orally or transdermally). In one embodiment, the donepezil given orally is a salt form of donepezil and the donepezil given transdermally is donepezil base. In one embodiment, the number of gastrointestinal related adverse events is between 2-5, 2-4, and 2-3 fold lover, and in another embodiment, the number of gastrointestinal related adverse events is at least about two-fold, at least about three-fold, at least about four-fold, or at least about five-fold lower than subjects treated with the same dose of donepezil orally. In one embodiment, the delivery of donepezil is for the treatment of Alzheimer's disease.

IV. Examples

The following examples are illustrative in nature and are in no way intended to be limiting.

Example 1

Donepezil Transdermal Delivery System

A transdermal delivery system comprising donepezil was prepared as follows.

Preparation of drug reservoir: 1.20 grams of sorbitan monolaurate (SPAN® 20) was dissolved in 6.00 g of triethyl citrate and mixed with 1.80 grams of lauryl lactate and 89.69 grams of ethyl acetate. 6.00 grams of glycerin was added and mixed. 9.00 grams of donepezil hydrochloride and 1.82 grams of sodium bicarbonate were added and dispersed in the mixture. 12.00 grams of crosslinked, micronized polyvinylpyrrolidone (Kollidon® CL-M) was then added and the mixture was homogenized. To the homogenized drug dispersion, 43.93 grams of acrylic acid/vinyl acetate copolymer (Duro-Tak® 387-2287, solid content 50.5%) was added and well mixed. The wet adhesive formulation was coated on a release liner and dried using a lab coater (Werner Mathis) to yield a dry coat weight of 12 $mg/cm^2$.

Preparation of contact adhesive: 0.60 grams of sorbitan monolaurate (SPAN® 20) was dissolved in 3.0 grams of triethyl citrate and mixed with 0.9 grams of lauryl lactate, 25.45 grams of ethyl acetate and 1.34 grams of isopropyl alcohol. 6.00 grams of crosslinked, micronized polyvinylpyrrolidone (Kollidon® CL-M) was added and the mixture was homogenized. To the homogenized mixture 38.61 grams of acrylic acid/vinyl acetate copolymer (Duro-Tak® 387-2287, solid content 50.5%) was added and mixed well. The wet adhesive formulation was coated on a release liner and dried to give a dry coat weight of 5 $mg/cm^2$.

Lamination and die-cut: A rate controlling membrane (CELGARD® 2400 or Reemay® 2250) was laminated on the adhesive side of the drug reservoir. Then the contact adhesive was laminated on top of the rate controlling membrane laminated with drug reservoir. The release liner on the drug reservoir side was replaced and laminated with backing film. The final five layer laminate was die-cut into transdermal patches.

The weight percentage of the components in the transdermal delivery system are set forth in Table 1.1 below.

TABLE 1.1

| Ingredient | wt. % in drug reservoir | wt. % in contact adhesive | total wt. % in delivery system |
|---|---|---|---|
| Donepezil HCl | 5.2% | — | 3.6% |
| Sodium bicarbonate | 1.1% | — | 0.74% |
| sorbitan monolaurate (Span ® 20) | 0.7% | 0.8% | 0.73% |
| Triethyl citrate | 3.5% | 3.9% | 3.6% |
| Lauryl lactate | 1.05% | 1.2% | 1.1% |
| Ethyl acetate | 52.3% | 33.5% | 46.6% |
| Glycerin | 3.5% | — | 2.4% |
| crosslinked, micronized polyvinylpyrrolidone (Kollidon ® CL-M) | 7.0% | 7.9% | 7.3% |
| acrylic acid/vinyl acetate copolymer (Duro-Tak ® 387-2287) | 25.6% | 50.9% | 33.4% |
| isopropyl alcohol | — | 1.8% | 0.54% |

Example 2

Donepezil Transdermal Delivery Systems

Transdermal delivery system comprising donepezil was prepared as follows.

Preparation of drug reservoir: Sorbitan monolaurate (SPAN® 20) was dissolved in triethyl citrate and mixed with lauryl lactate. Glycerin was added and mixed. Donepezil hydrochloride and sodium bicarbonate were added and dispersed in the mixture. Crosslinked, micronized polyvinylpyrrolidone (KOLLIDON® CL-M) was then added and the mixture was homogenized. To the homogenized drug dispersion, acrylic acid/vinyl acetate copolymer (DURO-TAK® 387-2287, solid content 50.5%) was added and well mixed. The wet adhesive formulation was coated on a release liner and dried using a lab coater (Werner Mathis).

Preparation of contact adhesive: Sorbitan monolaurate (SPAN® 20) was dissolved in triethyl citrate and mixed with lauryl lactate. Crosslinked, micronized polyvinylpyrrolidone (Kollidon® CL-M) was added and the mixture was homogenized. To the homogenized mixture acrylic acid/vinyl acetate copolymer (DURO-TAK® 387-2287, solid content 50.5%) was added and mixed well. The wet adhesive formulation was coated on a release liner and dried.

Lamination and die-cut: A polypropylene microporous membrane (Celgard® 2400) was pretreated by coating it with a solvent mixture of sorbitan monolaurate, triethyl citrate and lauryl lactate to saturate the membrane with the solvent mixture. The pretreated membrane was laminated on the adhesive side of the drug reservoir. Then the contact adhesive was laminated on top of the rate controlling membrane laminated with drug reservoir. The release liner on the drug reservoir side was replaced and laminated with backing film. The final five layer laminate was die-cut into transdermal patches.

The weight percentage of the components in the transdermal delivery systems are set forth in Table 2.1 below.

TABLE 2.1

| Ingredient | Drug Reservoir (Dry Formula % wt/wt) | Contact Adhesive (Dry formula, % wt/wt) |
| --- | --- | --- |
| Donepezil HCl | 16.0 | 0 |
| Sodium bicarbonate | 2.6 | 0 |
| Triethyl citrate | 10.0 | 10.0 |
| Lauryl Lactate | 3.0 | 3.0 |
| Sorbitan monolaurate (SPAN® 20) | 2.0 | 2.0 |
| Glyerine | 10.0 | 0 |
| PVP-CLM (KOLLIDONE®-CLM) | 15.0 | 20.0 |
| acrylic acid/vinyl acetate copolymer (Duro-Tak® 387-2287) | 41.4 | 65.0 |

Example 3

Donepezil Transdermal Delivery Systems

Transdermal delivery system comprising donepezil was prepared as follows.

Preparation of drug reservoir: Sorbitan monolaurate (SPAN® 20) was dissolved in triethyl citrate and mixed with lauryl lactate. Glycerin was added and mixed. Donepezil hydrochloride was added and dispersed in the mixture. Fumed silica (AEROSIL® 200 Pharma) was then added and the mixture was homogenized. To the homogenized drug dispersion, acrylic acid/vinyl acetate copolymer (DURO-TAK® 387-2287, solid content 50.5%) and dimethylaminoethyl methacrylate, butyl methacrylate, methyl methacrylate copolymer (EUDRAGIT® EPO) were added and well mixed. The wet adhesive formulation was coated on a release liner and dried using a lab coater (Werner Mathis).

Preparation of contact adhesive: Sorbitan monolaurate (SPAN® 20) was dissolved in triethyl citrate and mixed with lauryl lactate. Crosslinked, micronized polyvinylpyrrolidone (KOLLIDON® CL-M) was added and the mixture was homogenized. To the homogenized mixture acrylic acid/vinyl acetate copolymer (Duro-Tak® 387-2287, solid content 50.5%) added and mixed well. The wet adhesive formulation was coated on a release liner and dried.

Lamination and die-cut: A polypropylene microporous membrane (Celgard® 2400) was pretreated by coating it with a solvent mixture of sorbitan monolaurate, triethyl citrate and lauryl lactate to saturate the membrane with the solvent mixture. The pretreated membrane was laminated on the adhesive side of the drug reservoir. Then the contact adhesive was laminated on top of the rate controlling membrane laminated with drug reservoir. The release liner on the drug reservoir side was replaced and laminated with backing film. The final five layer laminate was die-cut into transdermal patches.

The weight percentage of the components in the transdermal delivery systems are set forth in Table 3.1 below.

TABLE 3.1

| Ingredient | Drug Reservoir (Dry Formula % wt/wt) | Contact Adhesive (Dry formula, % wt/wt) |
| --- | --- | --- |
| Donepezil HCl | 25.0 | 0 |
| dimethylaminoethyl methacrylate, butyl methacrylate, methyl methacrylate copolymer (EUDRAGIT ® EPO) | 17.7 | 0 |
| Triethyl citrate | 10.0 | 10.0 |
| Lauryl Lactate | 6.0 | 6.0 |
| Sorbitan monolaurate (SPAN ® 20) | 2.0 | 2.0 |
| fumed silica (AEROSIL ® 200 Pharma) | 7.0 | 0 |
| Glyerine | 10.0 | 0 |
| PVP-CLM (KOLLIDONE ®-CLM) | 0 | 20.0 |
| acrylic acid/vinyl acetate copolymer (Duro-Tak ® 387-2287) | 24.3 | 64.0 |

Example 4

In Vivo Administration of Donepezil from a Donepezil Transdermal Delivery System Transdermal delivery systems comprising donepezil were prepared as described in Example 1. Twelve (12) human subjects were randomized into two groups for treatment with a transdermal delivery system (n=6) or with orally administered donepezil (ARICPET®), 5 mg taken on day one and on day 7 of the study. The transdermal delivery system was applied to the skin and worn for one week and then removed. Blood samples were taken daily from the subjects treated with the transdermal delivery system. Blood samples were taken at frequent hour intervals on day 1 and day 7 in the group treated with orally delivered donepezil, and again on days 8, 10, 12 and 14. Mean plasma concentration of donepezil in the treatment groups are shown in FIGS. 2A-2B.

Example 5

In Vivo Administration of Donepezil from a Donepezil Transdermal Delivery System Transdermal delivery systems comprising donepezil were prepared as described in Example 2. Patients were enrolled and randomly separated into three treatment arms for a five week treatment study. The patients in Arm 1 (n=52) and Arm 2 (n=51) were treated with a transdermal system of Example 2, where the patients in Arm 1 wore a patch having a smaller surface area (Patch A) than the patients in Arm 2 (Patch B). Other than size, Patch A and Patch B were identical. In the first week of the study, patients in Arm 1 and Arm 2 wore patches designed to deliver 5 mg donepezil from a once-weekly patch. After the initial 7 day period, the patients were given a transdermal system designed to be worn for 7 days (once-weekly transdermal patch) to deliver 10 mg donepezil per day, again with Patch A differing from Patch B only in surface area. The transdermal systems were replaced weekly for 4 weeks. The patients in Arm 3 (n=54) were treated with a daily oral dose of 5 mg donepezil (ARICEPT) for 7 days followed by a once daily 10 mg dose of donepezil (ARICEPT) for 4 weeks.

For the subjects in Arm 1 and Arm 2, blood samples were taken daily during the fourth week of dosing at the 10 mg level, when plasma concentrations were at steady state. For the subjects in Arm 3, blood samples were taken on the last day of the fourth week of 10 mg/day dosing. The mean plasma concentration of donepezil for the treatment arms in the fourth week of the 10 mg dosing are shown in FIG. 5A, where subjects treated with donepezil administered transdermally from transdermal Patch A (smaller surface area, solid line, transdermal Patch B (larger surface area, dashed line) and oral donepezil (thick, bold line at days 6-7) are shown, along with a dotted line showing the projected daily plasma concentration for oral treatment.

FIG. 5B is a bar graph showing the number of gastrointestinal related adverse events (nausea, vomiting and diarrhea) reported by subjects in the study, where bars with dashed fill correspond to subjects treated with the weekly smaller size transdermal patch, the bars with vertical line fill correspond to subjects treated with the weekly larger size transdermal patch, and the bars with horizontal line fill correspond to the subjects treated with oral donepezil.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

It is claimed:

1. A composition, comprising:
a drug reservoir comprising (i) donepezil base generated in situ in the drug reservoir by reaction of donepezil HCl and a pharmaceutically acceptable alkaline salt selected from sodium bicarbonate and potassium bicarbonate, said donepezil HCl and said alkaline salt present in the drug reservoir in an equimolar or less than equimolar ratio of alkaline salt to donepezil HCl; (ii) glycerine; and (iii) an acrylate copolymer, wherein the donepezil base is generated for a period of between about 3-10 days in an amount that provides a therapeutically effective dose of donepezil base to a human for the period.

2. The composition of claim 1, wherein the drug reservoir further comprises triethyl citrate or sorbitan monolaurate.

3. The composition of claim 1, wherein the drug reservoir comprises an acrylic acid/vinyl acetate copolymer adhesive and a crosslinked polyvinylpyrrolidone.

4. A composition, comprising:
a drug reservoir consisting essentially of donepezil base generated in situ in the drug reservoir by reaction of a molar amount of donepezil HCl and an equimolar or less than equimolar amount of sodium bicarbonate; a solvent composition comprising one or more of triethyl citrate, lauryl lactate, sorbitan monolaurate, and glycerin; crosslinked polyvinylpyrrolidone and an acrylate copolymer, wherein donepezil base is generated for a period of between about 3-10 days in an amount that provides a therapeutically effective dose of donepezil base to a human for the period.

5. A composition, comprising:
a drug reservoir consisting essentially of:
(a) donepezil base generated in situ for a period of between about 3-10 days in the drug reservoir by reaction of between about 5-25 wt % donepezil HCl and between about 1-5 wt % sodium bicarbonate, said donepezil HCl and said sodium bicarbonate present in the drug reservoir in an equimolar or less than equimolar ratio of sodium bicarbonate to donepezil HCl;
(b) about 0-15 wt % triethyl citrate;
(c) about 0-5 wt % sorbitan monolaurate
(d) about 5-15 wt % glycerin;
(e) about 1-10 wt % lauryl lactate;
(f) about 5-25 wt % crosslinked polyvinylpyrrolidone; and
(g) about 30-65 wt % acrylate-vinylacetate copolymer.

6. A composition, comprising:
a drug reservoir consisting essentially of:
(a) donepezil base generated in situ for a period of between about 3-10 days in the drug reservoir by reaction of between about 10-18 wt % donepezil HCl and an equimolar or less than equimolar amount of sodium bicarbonate, wherein the weight percent of sodium bicarbonate in the drug reservoir is between about 1-5 wt %;
(b) about 8-12 wt % triethyl citrate;
(c) about 1.5-2.5 wt % sorbitan monolaurate
(d) about 9-11 wt % glycerin;
(e) about 1-10 wt % lauryl lactate;
(f) about 13-17 wt % crosslinked polyvinylpyrrolidone; and
(g) about 40-42 wt % acrylate-vinylacetate copolymer.

7. The composition of claim 1, further comprising a contact adhesive layer.

8. The composition of claim 7, further comprising an intermediate layer positioned between the contact adhesive layer and the drug reservoir.

9. The composition of claim 1, wherein the amount of donepezil base generated is an amount that yields a plasma concentration bioequivalent to oral administration of donepezil hydrochloride at a daily dose selected from 5 mg, 10 mg, and 23 mg.

10. The composition of claim 1, wherein the amount of donepezil base generated is an amount that yields at approximately steady state a transdermal plasma concentration bioequivalent to oral administration of donepezil hydrochloride at a daily dose selected from 5 mg, 10 mg, and 23 mg.

11. The composition of claim 1, wherein the amount of donepezil base is generated continuously over the period to provide a therapeutically effective dose of between about 1-25 mg/day.

12. The composition of claim 1, wherein greater than about 10 wt % donepezil HC is present in the drug reservoir and an equimolar or less than equimolar amount of the pharmaceutically acceptable alkaline salt, wherein the weight percent of alkaline salt in the drug reservoir is between about 2-5 wt %.

13. The composition of claim 1, wherein greater than about 14 wt % donepezil HC is present in the drug reservoir and the pharmaceutically acceptable alkaline salt is present at about 2.6 wt % or less.

14. The composition of claim 1, wherein donepezil HCl and the pharmaceutically acceptable alkaline salt are present in the drug reservoir in an equimolar amount or at a molar ratio of 0.82.

* * * * *